(12) United States Patent
Gharavi et al.

(10) Patent No.: US 10,358,678 B2
(45) Date of Patent: Jul. 23, 2019

(54) METHODS FOR IDENTIFYING SUBJECTS WITH A GENETIC RISK FOR DEVELOPING IGA NEPHROPATHY

(71) Applicants: Ali Gharavi, New York, NY (US); Krzysztof Kiryluk, New York, NY (US); Richard Lifton, North Haven, CT (US)

(72) Inventors: Ali Gharavi, New York, NY (US); Krzysztof Kiryluk, New York, NY (US); Richard Lifton, North Haven, CT (US)

(73) Assignees: The Trustees of Columbia University in the City of New York, New York, NY (US); Yale University, New Haven, CT (US)

( * ) Notice: Subject to any disclaimer, the term of this patent is extended or adjusted under 35 U.S.C. 154(b) by 0 days.

(21) Appl. No.: 15/437,147

(22) Filed: Feb. 20, 2017

(65) Prior Publication Data

US 2017/0226586 A1 Aug. 10, 2017

Related U.S. Application Data

(62) Division of application No. 14/000,328, filed as application No. PCT/US2012/025742 on Feb. 17, 2012, now Pat. No. 9,598,733.

(60) Provisional application No. 61/444,583, filed on Feb. 18, 2011, provisional application No. 61/444,126, filed on Feb. 17, 2011.

(51) Int. Cl.
C12Q 1/6883 (2018.01)

(52) U.S. Cl.
CPC ...... *C12Q 1/6883* (2013.01); *C12Q 2600/112* (2013.01); *C12Q 2600/136* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | |
|---|---|---|
| 5,139,932 A | 8/1992 | Cederholm et al. |
| 6,429,024 B1 | 8/2002 | Kokubo et al. |
| 6,962,984 B2 | 11/2005 | Ishiwata et al. |
| 7,521,190 B2 | 4/2009 | Jones et al. |
| 2008/0152659 A1 | 6/2008 | Hageman |
| 2009/0029908 A1 | 1/2009 | Mukherjee et al. |
| 2009/0258822 A1 | 10/2009 | Hageman |
| 2009/0312394 A1 | 12/2009 | Hughes |
| 2010/0009368 A1 | 1/2010 | Young |
| 2010/0297660 A1 | 11/2010 | Winkler et al. |
| 2011/0020810 A1 | 1/2011 | Winn et al. |
| 2011/0318738 A1 | 12/2011 | Jones et al. |

FOREIGN PATENT DOCUMENTS

| | | |
|---|---|---|
| RU | 2269297 C1 | 2/2006 |
| WO | 98/32849 A2 | 7/1998 |
| WO | 2003/000842 A2 | 1/2003 |
| WO | 2010/038974 A2 | 4/2010 |

OTHER PUBLICATIONS

Feehally et al. J Ann Soc Nephrol. 2010. 21:1791-1797. (Year: 2010).*
dbSNP. Retrieved on Jul. 12, 2018 from the internet: https://www.ncbi.nlm.nih.gov/projects/SNP/snp_ref.cgi?rs=6677604. (Year: 2018).*
Remen et al., "Gene Gain and Loss During Evolution of Obligate Parasitism in the White Rust Pathogen of Arabidopsis: *Albugo laibachii* Alem 1, Genomic Contig", Apr. 12, 2011, Publisher: GenBank, Published in: http://www.ncbi.nlm.nih.gov/pubmed/21750662.
Rensing, S.A. et al., "The *Physcomitrella* Genome Reveals Evolutionary Insights Into the Conquest of Land by Plants", May 22, 2009, pp. 64-69, vol. 319, No. 5859, Publisher: NCBI, Published in: http://www.ncbi.nlm.nih.gov/pubmed/18079367.
Zhou, X., et al, "HLA-DPB1 and DPB2 Are Genetic Loci for Systemic Sclerosis: A genome-wide association study in Koreans with replication in North Americans," Arthritis and Rheumatism 2009, pp. 3807-3814, vol. 60, No. 12, Publisher: John Wiley and Sons, Published in: http://onlinelibrary.wiley.com/doi/10.1002/art.24982/abstract.
Sanna-Cherchi, S., et al., "Renal Outcome in Patients With Congential Anomalies of the Kidney and Urinary Tract", Jun. 17, 2009, pp. 528-533, vol. 76, Publisher: Kidney Intenational, Published in: http://www.ncbi.nlm.nih.gov/pubmed/19536081.
Sanna-Cherchi, S., et al., "Localization of a Gene for Nonsyndromic Renal Hypodysplasia to Chromosome 1p32-33," The American Journal of Human Genetics 2007, pp. 539-549, vol. 80, Issue 3.
Sanna-Cherchi, S., et al., "Genetic approaches to human renal agenesis/hypoplasia and dysplasia," Pediatr. Nephrol, 2007, pp. 1675-1684, vol. 22.
Sanna-Cherchi, S., et al. "Copy-Number Disorders Are a Common Cause of Congenital Kidney Malformations." The American Journal of Human Genetics, pp. 987-997, vol. 91. Dec. 7, 2012.
Schedl, A., "Renal abnormalities and their developmental origin," Nat. Rev. Genet, 2007; pp. 791-802, vol. 8.
Singer, J.B., et al., "A genome-wide study identifies HLA alleles associated with lumiracoxib-related liver injury," Nature Genetics 2010, pp. 711-714, vol. 42, No. 8, Publisher: Nature Publishing Group, Published in: http://www.nature.com/ng/journal/v42/n8/fulling.632.html.

(Continued)

*Primary Examiner* — Joseph G. Dauner
(74) *Attorney, Agent, or Firm* — Beusse Wolter Sanks & Maire, PLLC; Judith Evans; Timothy H. Van Dyke

(57) ABSTRACT

Seven protective alleles for IgA nephropathy have been discovered that can be identified by analyzing a DNA sample for seven respective SNPs. A method is provided for identifying and treating subjects at risk of developing IgA neuropathy based on a new seven-SNP genetic risk score. Also provided are screening methods to identify compounds that bind to and reduce the expression or biological activity of a either CFHR1 or CFHR3.

7 Claims, 6 Drawing Sheets

(56) References Cited

OTHER PUBLICATIONS

Song, R., et al., "Genetics of Congenital Anomalies of the Kidney and Urinary Tract", 2011, pp. 353-364, vol. 26, Publisher Pediatr Nephrol, Published in: http://www.ncbi.nlm.nih.gov/pubmed/20798957.

Suzuki, H., et al., "The Pathophysiology of IgA Nephropathy," Journal of the American Society of Nephrology 2011, pp. 1795-1803, vol. 22, No. 10, Publisher: American Society of Nephrology, Published in: http://jasn.asnjournals.org/content/22/10/1795.long.

Tashiro, H., et al., "NEDO Human cDNA Sequencing Project: Unnamed Protein Product (*Homosapiens*)", Jan. 9, 2008, Publisher GenBank, Published in: http://www.ncbi.nlm.nih.gov/sviewer/viewer.fcgi?noredirect=1&db=protein&val=BAF83774.1.

Wang, K., et al., "Penn CNV: an integrated hidden Markov model designed for high-resolution copy number variation detection in whole-genome SNP genotyping data," Genome Res., 2007, pp. 1665-1674, vol. 17.

Weber, S., et al., "Prevalence of mutations in renal developmental genes in children with renal hypodysplasia: results of the ESCAPE study," J. Am. Soc. Nephrol, 2006, pp. 2864-2870, vol. 17.

Weng, P.L., et al., "A Recessive Gene for Primary Vesicoureteral Reflux Maps to Chromosome 12p11-q13," J Am Soc Nephrol 2009, pp. 1633-1640, vol. 20.

Xie, J., et al., "Predicting Progression of IgA Nephropathy: New Clinical Progression Risk Score," PLoS One 2012, pp. 1-9, vol. 7, No. 6, Publisher: Public Library of Science, Published in: http://www.plosone.org/article/fetchObject.action?uri=info%3Adoi%2F10.1371%2Fjournal.pone.0038904&representation=PDF.

Xie, J., et al., "Fine Mapping Implicates a Deletion of CFHR1 and CFHR3 in Protection from IgA Nephropathy in Han Chinese," J Am Soc Nephrol 2016, pp. 3187-3194, vol. 27.

Yu, X.Q., et al., "A genome-wide association study in Han Chinese identifies multiple susceptibility loci for IgA nephropathy," Nature Genetics 2012, pp. 178-182, vol. 44, No. 2, Publisher: Nature Publishing Group, Published in: http://www.nature.coming/journal/v44/n2/fulling.1047.html.

Zhao, H., et al., "Role of fibroblast growth factor receptors 1 and 2 in the ureteric bud," Developmental Biology, 2004, pp. 403-415, vol. 276.

NCBI Reference Sequence: NM_015375.2 "*Homo sapiens* dual serine/threonine and tyrosine protein kinase (DSTYK), transcript variant 1, mRNA"; Aug. 5, 2014.

NCBI Reference Sequence: XP_001765144.1 "Qa-SNARE, Sso1/Syntaxin1-type, SYP12A-group [Physcomirella patens]"; Aug. 29, 2014.

Genbank: BAC87313.1 "Unnamed Protein Product [*Homo sapiens*]"; Aug. 29, 2014.

Genbank: FR833085.1 "Albugo laibachii Alem1, genomic contig CONTIG_87_Em1_cons_v4_86971_235_62031"; Mar. 29, 2014.

Abe, G., et al., "Function of FGF signaling in the developmental process of the median fin fold in zebrafish," Dev. Biol., 2007, pp. 355-366, vol. 304.

Barrat, J., et al., "IgA Nephropathy," Journal of the American Society of Nephrology 2005, pp. 2088-2097, vol. 16, No. 7, Publisher: American Society of Nephrology, Published in: http://jasn.asnjournals.org/content/16/7/2088.full.

Bates, C.M., "Role of fibroblast growth factor receptor signaling in kidney development," American Journal of Physiology Renal Physiology, 2011, pp. F245-F251, vol. 301.

Beerman, I., et at al., "The genetics of IgA nephropathy," Nat Clin Pract Nephrol 2007, pp. 325-328, vol. 6, No. 3, Publisher: Nature Publishing Group, Published in: http://www.nature.com/nrneph/journal/v3/n6/full/ncpneph0492.html.

Bisceglia, L., et al., "Genetic Heterogeneity in Italian Families with IgA Nephropathy: Suggestive Linkage for Two Novel IgA Nephropathy Loci," American Journal of Human Genetics 2006, pp. 1130-1134, vol. 79, No. 6, Publisher: The American Society of Human Genetics, Published in: http://www.ncbi.nlm.nih.govipubmed/17186473.

Burton, P., et al., "Genome-wide association study of 14,000 cases of seven common diseases and 3,000 shared controls," Nature 2007, pp. 661-678, vol. 447, Publisher: Nature Publishing Group, Published in: http://www.nature.com/nature/journal/v447/n7145/abs/nature05911.html.

Corson, L.B., et al., "Spatial and temporal patterns of ERK signaling during mouse embryogenesis," Development, 2003, pp. 4527-4537, vol. 130.

Craddock, N. et al., "Genome-wide association study of CNVs in 16,000 cases of eight common diseases and 3,000 shared controls," Nature 2010, pp. 713-720, vol. 464, Publisher: Nature Publishing Group.

Davila, S., et al., "Genome-wide association study identifies variants in the CFH region associated with host susceptibility to meningococcal disease," Nature Genetics 2010, pp. 772-776, vol. 42, No. 9, Publisher: Nature Publishing Group, Published in: http://www.nature.com/ng/journal/v42/n9/full/ng.640.html.

Debakker, P.I., et al., "A high-resolution HLA and SNP haplotype map for disease association studies in the extended human MHC," Nature Genetics 2006, pp. 1166-1172, vol. 38, No. 10, Publisher: Nature Publishing Group, Published in: http://www.nature.com/ng/journal/v38/n10/full/ng1885.html.

Ellington, A.D. and Szostak, J.W., "Selection in vitro of single-stranded DNA molecules that fold into specific ligand-binding structures," Nature 1992, pp. 850-852, vol. 355.

Feehally, J., et al., "HLA Has Strongest Association with IgA Nephropathy in Genome-Wide Analysis," Journal of the American Society of Nephrology 2010, pp. 1791-1797, vol. 21, No. 10, Publisher: The American Society of Nephrology, Published in: http://jasn.asnjournals.org/content/21/10/1791.full.pdf+html.

Feehally, J, et al., "Genome-Wide Analysis Identifies Strong Association Between HLA and IgA Nephropathy," J Am Soc Nephrol 2010, pp. 1-7.

Genetics Home Reference, "Genetic Conditions—Atypical hemolytic-uremic syndrome," http://ghr.nlm.gov/condition/atypical-hemolytic-uremic-syndrome, retrieved on Jul. 18, 2012, pp. 1-5.

Gharavi, A.G., et al., "IgA nephropathy, the most common cause of glomerulonephritis, is linked to 6q2223," Nature Genetics 2000, pp. 354-357, vol. 26, Publisher: Nature Publishing Group, Published in: http://www.nature.com/ng/journal/v26/n3tfull/ng1100_354.html.

Gharavi, A.G., et al., "Aberrant IgA1 Glycosylation Is Inherited in Familial and Sporadic IgA Nephropathy," Journal of the American Society of Nephrology 2008, pp. 1008-1014, vol. 19, No. 5, Publisher: The American Society of Nephrology, Published in: http://jasn.asnjournals.org/content/19/5/1008.full.pdf.

Gharavi, A.G., et al., "Genome-wide association study identifies susceptibility loci for IgA nephropathy", "Nature Genetics", 2011, pp. 321-327, vol. 43, Publisher: Nature Publishing Group, Published in: http://www.nature.com/ng/journal/v43/n4tfulling.787.html.

Griffin, K.J., et al., "Interplay between FGF, one-eyed pinhead, and T-box transcription factors during zebrafish posterior development," Dev. Biol., 2003, pp. 456-466, vol. 264.

Gudbjartsson, D.F., et al., "Allegro, a new computer program for multipoint linkage analysis," Nat. Genet, 2000, pp. 12-13, vol. 25.

Gusev, A., et al., "Whole population, genome-wide mapping of hidden relatedness," Genome Research 2009, pp. 318-326, vol. 19, Publisher: Cold Spring Harbor Laboratory Press, Published in: http://genome.cshlp.org/content/19/2/318.long.

Hastings, M.C., et al., "Galactose-Deficient IgA1 in African Americans with IgA Nephropathy: Serum Levels and Heritability," Journal of the American Society of Nephrology 2010, pp. 2069-2074, vol. 5, No. 11, Publisher: American Society of Nephrology, Published in: http://cjasn.asnjoumals.org/content/5/11/2069.full.pdf.

Hermann, T. and Patel, D.J., "Adaptive recognition by nucleic acid aptamers," Science 2000, pp. 820-825, vol. 287.

Hsu, S., "Evidence for genetic factors in the development and progression of IgA nephropathy," Kidney International 2000, pp. 1818-1835, vol. 57, No. 5, Publisher: Nature Publishing Group, Published in: http://www.nature.com/ki/journal/v57/n5/pdf/4491515a.pdf.

(56) References Cited

OTHER PUBLICATIONS

Hughes, A.E., et al., "A common CFH haplotype, with deletion of CFHR1 and CFHR3, is associated with lower risk of age-related macular degeneration," Nature Genetics 2006, pp. 1173-1173, vol. 38, No. 10, Publisher: Nature Publishing Group, Published in: http://www.nature.com/ng/journal/v38/n10/full/ng1890.html.
IGA Nephropathy Support Network, "About the IgA Nephropathy Support Group," retrieved on Jul. 18, 2012, pp. 1-3.
ISA/US: International Search Report and Written Opinion, International Patent Application No. PCT/US12/025742, dated Sep. 24, 2012, pp. 1-6.
ISA/US: International Search Report and Written Opinion, International Patent Application No. PCT/US14/34056, dated Sep. 22, 2014, pp. 1-10.
Kamatani, Y., et al., "A genome-wide association study identifies variants in the HLA-DP locus associated with chronic hepatitis B in Asians," Nature Genetics 2009, pp. 591-595, vol. 41, No. 5, Publisher: Nature Publishing Group, Published in: http://www.nature.com/ng/journal/v41/n5/pdf/ng.348.pdf.
Kim, Y., et al., "Uteroglobin gene polymorphisms affect the progression of immunoglobulin A nephropathy by modulating the level of uteroglobulin expression," Pharmacogenetics 2001, pp. 299-305, vol. 11, No. 4, Publisher: Nature Publishing Group, Published in: http://www.ncbi.nlm.nih.gov/pubmed/11434507.
Kiryluk, K., et al., "Discovery of new risk loci for IgA nephropathy implicates genes involved in immunity against intestinal pathogens," Nature Genetics 2014, pp. 1187-1196, vol. 46, No. 11.
Kiryluk, K. and Novak, J., "The genetics and immunobiology of IgA nephropathy," J Clin Invest. 2014, pp. 2325-2332, vol. 124, No. 6.
Kiryluk, K., "Genetic Susceptibility, HIV Infection, and the Kidney," Journal of the American Society of Nephrology 2007, pp. S25-S35, vol. 2, Publisher: American Society of Nephrology, Published in: http://cjasn.asnjournals.org/content/2/Supplement_1/S25.full.pdf.
Kiryluk, K., et al., "Genetic studies of IgA nephropathy: past, present, and future," Pediatric Nephrology 2010, pp. 2257-2268, vol. 25, No. 11, Publisher: International Pediatric Nephrology Association, Published in: http://link.springer.com/article/10.1007%2Fs00467-010-1500-7.
Kiryluk, K., et al., "IgA nephropathy the case for a genetic basis becomes stronger," Nephrology Dialysis Transplantation 2010, pp. 336-338, vol. 25, No. 2, Publisher: Oxford Journals, Published in: http://ndt.oxfordjournals.org/content/25/2/336.full.pdf.
Kiryluk, K., et al., "Aberrant glycosylation of IgA1 is inherited in both pediatric IgA nephropathy and HenochSchoenlein purpura nephritis," Kidney International 2011, pp. 79-87, vol. 80, No. 1, Publisher: Nature Publishing Group, Published in: http://www.nature.com/ki/journal/v80/n1/full/ki201116a.html.
Kiryluk, K., et al, "Geographic Differences in Genetic Susceptibility to IgA Nephropathy: GWAS Replication Study and Geospatial Risk Analysis," PLOS Genetics 2012, pp. 1-16, vol. 8, No. 6, Publisher: Public Library of Science, Published in: http://www.plosgenetics.org/article/fetchObject.action?uri=info%3Adoi%2F10.1371%2Fjournal.pgen.1002765&representation=PDF.
Kiryluk, K., et al., "Pathogenesis of immunoglobulin A nephropathy: recent insight from genetic studies," Annual Review of Medicine 2013, pp. 339-356, vol. 64, Publisher: Annual Reviews, Published in: http://www.annualreviews.org/doi/abs/10.1146/annurev-med-041811-142014?url_ver=Z39.88/2003&rfr_dat=cr_pub%3Dpubmed&rfr id=ori%3Arid%3Acrossreforg&jou.
Li, X., et al., "Advances in molecular genetics research of IgA nephropathy," Journal of Central South University Medical Sciences 2011, pp. 1120-1124, vol. 36, No. 11, Publisher: Central South University, Published in: http://xbyx.xysm.net/xbwk/fileup/PDF/2011111120.pdf.
Li, G., et al., "Variants of C1GALT1 gene are associated with the genetic susceptibility to IgA nephropathy," Kidney International 2007, pp. 448-453, vol. 71.
Lin, X., et al., "Aberrant galactosylation of IgA1 is involved in the genetic susceptibility of Chinese patients with IgA nephropathy," Nephrology Dialysis Transplant 2009, pp. 3372-3375, vol. 24, No. 11, Publisher: Oxford Journals, Published in: http://ndt.oxfordjournals.org/content/24/11/3372.full.pdf.
Maillard, N., et al., "Current Understanding of the Role of Complement in IgA Nephropathy," J Am Soc Nephrol 2015, pp. 1503-1512, vol. 26.
Malik, T.H., et al., "A Hybrid CFHR3-1 Gene Causes Familial C3 Glomerulopathy," J Am Soc Nephrol 2012, pp. 1155-1160, vol. 23.
Moldoveanu, M., et al., "Patients with IgA nephropathy have increased serum galactose-deficient IgA1 levels," Kidney International 2007, pp. 1148-1154, vol. 71, No. 11, Publisher: Nature Publishing Group, Published in: http://www.nature.com/ki/journal/v71/n11/full/5002185a.html.
Moore, I., et al., "Association of factor H autoantibodies with deletions of CFHR1, CFHR3, CFHR4, and with mutations in CFH, CFI, CD46, and C3 in patients with atypical hemolytic uremic syndrome," Blood 2010, pp. 379-387, vol. 115, No. 2, Publisher: American Society of Hematology, Published in: http://bloodjournal.hematologylibrary.org/content/115/2/379.full.pdf.
Papeta, N.,et al., "APOL1 variants increase risk for FSGS and HIVAN but not IgA nephropathy," Journal of American Society of Nephrology 2011, pp. 1991-1996, vol. 22, No. 11, Publisher: American Society of Nephrology, Published in: http://jasn.asnjournals.org/content/22/11/1991.full.pdf.
Paterson, A., et al., "Genome-Wide Linkage Scan of a Large Family with IgA Nephropathy Localizes a Novel Susceptibility Locus to Chromosome 2q3," Journal of the American Society of Nephrology 2007, pp. 2408-2415, vol. 18, No. 8, Publisher: American Society of Nephrology, Published in: http://jasn.asnjournals.org/content/18/8/2408.full.pdf.
Peng, J., et al., "Dusty protein kinases: primary structure, gene evolution, tissue specific expression and unique features of the catalytic domain," Biochimica et Biophysica Acta 2006, pp. 562-572, vol. 1759, Nos. 11-12.
Poladia, D.P., et al., "Role of fibroblast growth factor receptors 1 and 2 in the metanephric mesenchyme," Developmental biology, 2006, pp. 325-39, vol. 291.
Raychaudhuri, S., et al., "Associations of CFHR1-CFHR3 deletion and a CFH SNP to age-related macular degeneration are not independent," Nature Genetics 2010, pp. 553-555, vol. 42, No. 7, Publisher: Nature Publishing Group, Published in: http://www.nature.com/ng/journal/v42/n7/full/ng0710-553.html.
Renkema, K.Y., et al., "Novel perspectives for investigating congenital anomalies of the kidney and urinary tract (CAKUT)," Nephrol Dial Transplant. 2011, pp. 3843-3851, vol. 26, No. 12.

\* cited by examiner

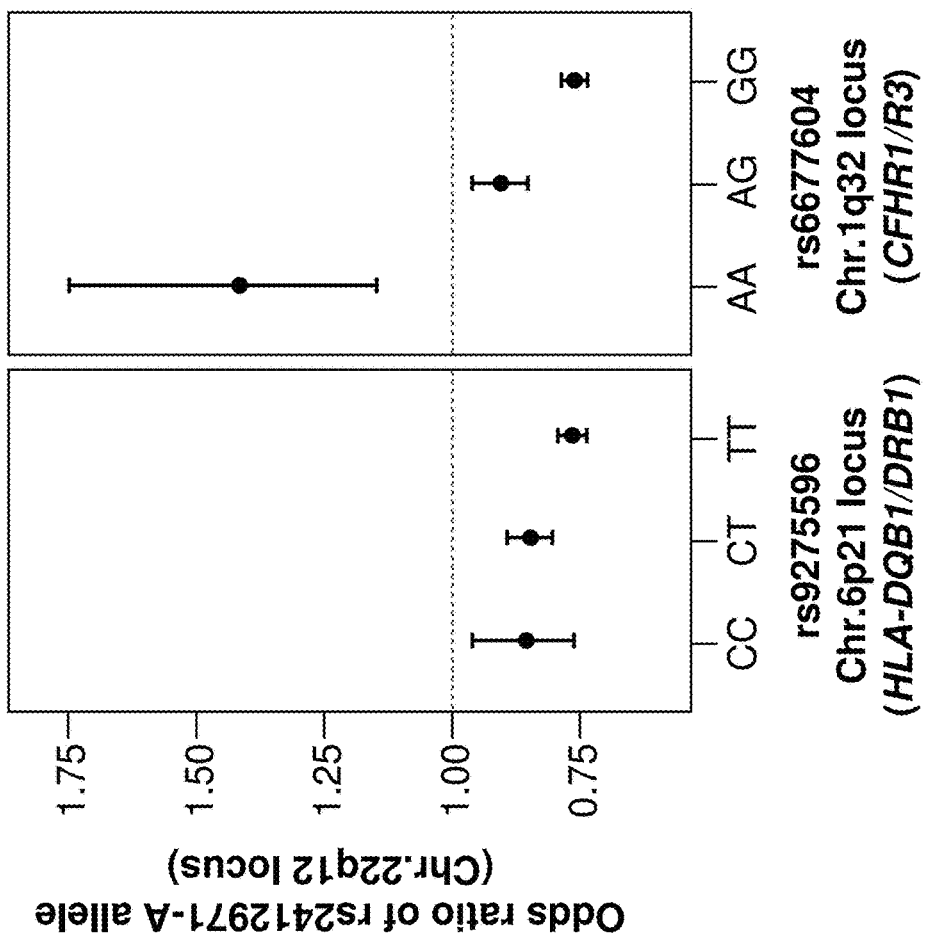

METHODS FOR IDENTIFYING SUBJECTS WITH A GENETIC RISK FOR DEVELOPING IGA NEPHROPATHY

CROSS-REFERENCE TO RELATED APPLICATIONS

This application is a divisional of U.S. application Ser. No. 14/000,328 filed Aug. 19, 2013, which is a national phase application of PCT Application No. PCT/US12/25742 filed Feb. 17, 2012 which claims benefit of Provisional Appln. 61/444,583, filed Feb. 18, 2011, and Provisional Appln. 61/444,126, filed Feb. 17, 2011, the entire contents of which are hereby incorporated by reference as if fully set forth herein, under 35 U.S.C. § 119(e).

STATEMENT OF GOVERNMENT INTEREST

The invention was made with Government support under DK087445 and DK082753 awarded by the National Institutes of Health. The Government has certain rights in the invention.

FIELD OF THE INVENTION

This in invention is in the field of genetic risk factors for kidney disease, specifically IgA nephropathy (IgAN).

BACKGROUND

Chronic kidney disease is a major cause of morbidity and mortality affecting 10-20% of the world population, with glomerulonephritis accounting for a significant proportion of cases[1-3]. IgA nephropathy (IgAN) is the most common form of glomerulonephritis and the most common cause of kidney failure among Asian populations[2,4]. The diagnosis of IgAN requires documentation by kidney biopsy demonstrating proliferation of the glomerular mesangium with deposition of immune complexes predominantly composed of Immunoglobulin A (IgA) and complement C3 proteins[3,5,6]. Registry data as well as autopsy and kidney-donor biopsy series suggest that there is a significant variation in prevalence among different ethnicities: IgAN is most frequent among Asians, with a disease prevalence as high as 3.7% detected among Japanese kidney donors[7], but is rare among individuals of African ancestry[5] and of intermediate prevalence among Europeans (up to 1.3%)[6].

The pathogenesis of IgAN is uncertain[8,9]. The finding of IgA1 glycosylation abnormalities among European, Asian, and African-American populations has suggested a shared pathogenesis among different groups[10-15]. Moreover, familial aggregation of IgAN has been reported among all ethnicities, suggesting a genetic component to disease[8,16]. To date linkage studies have identified several loci predisposing to IgAN, but underlying genes are not known[8,16-18]. A single, unreplicated genome-wide association study (GWAS) in a small European cohort (533 cases) has reported association of IgAN with the MHC complex[19].

Identifying specific mutations in one or more genes could be used as the basis for a noninvasive method to diagnose a predisposition to IgAN, and deciding which indications merit undergoing renal biopsy and prophylactic treatment.

SUMMARY OF THE INVENTION

Seven new protective alleles associated with identified SNPs have been identified that reduce a subject's risk of developing IgA nephropathy. Certain embodiments are directed to methods for determining if a subject has one or more protective alleles and hence a reduced risk of IgAN. This is accomplished by a. obtaining a DNA sample from the subject, b. analyzing the DNA sample to detect the presence of one or more SNPs selected from the group comprising [either rs6677604 or rs3766404], rs9275596, rs9275224, rs2856717, [either rs9357155 or rs2071543], [either rs1883414 or rs3129269] and [either rs2412971 or rs2412973], c. determining whether the sample has one or more SNPs, wherein each of the SNPs indicates a respective protective allele, and d. determining that the subject has a reduced risk of developing IgA nephropathy if the subject has at least one protective allele. The method above can further include calculating a genetic risk score comprising determining a weighted sum of the number of protected alleles in the DNA sample, multiplied by the log of the odds ratio for each of the individual protected alleles.

Another set of embodiments is directed to a method for determining whether or not to treat a subject by analyzing the DNA sample to detect the presence of one or more SNPs selected from the group comprising [either rs6677604 or rs3766404], rs9275596, rs9275224, rs2856717, [either rs9357155 or rs2071543], [either rs1883414 or rs3129269] and [either rs2412971 or rs2412973], determining whether the sample has one or more SNPs, wherein each of the SNPs indicates a respective protective allele, and treating the subject for IgAN if the subject does not have at least one protective allele. In an embodiment the treatment includes administering therapeutically effective amounts of one or more steroids.

Another set of embodiments is directed to methods for screening candidate compounds in a library to identify compounds that bind to CFHR1 and CFHR3 (target proteins); then providing the target protein; contacting the candidate compounds with the target protein under conditions suitable for binding of the compounds to the protein, screening the library of candidate compounds for a compound that has high affinity binding to the target protein; and if a compound binds to the target protein with high affinity, then determining if binding of the compound to the target protein reduces the biological activity of the target protein, and finally selecting the compound if it binds with high affinity to the target protein and thereby reduces the biological activity of the target protein. The compounds can be small molecules, peptides or antibodies and they are preferably bound to a solid support.

Another set of embodiments is directed to methods for treating or preventing IgAN in a subject by reducing the expression of CFHR1 or CFHR3, or both comprising administering therapeutically effective amounts of inhibitory oligonucleotides that reduce the expression of CFHR1 or CFHR3, or both.

Other embodiments are directed to microarrays comprising two or more oligonucleotides bound to a support that are complementary to and hybridize to one or more respective target oligonucleotide selected from the group comprising (i) rs6677604 (A), rs9275596 (C), rs9357155 (A), rs1883414 (T), rs2412971(A), rs9275224 (A) and rs2856717 (T); or (ii) rs3766404 (C), rs2856717 (T), rs2071543 (A), rs3129269 (T), rs2412973 (A), rs9275224 (A) and rs2856717 (T), wherein each of the SNPs indicates a respective protective allele. Preferably, the oligonucleotides bound to the support are complementary to and hybridize with the target oligonucleotides in the group consisting of [either rs6677604 or rs3766404], rs9275596, rs9275224, rs2856717, [either rs9357155 or rs2071543], [either rs1883414 or rs3129269] and [either rs2412971 or rs2412973].

These and other features, aspects, and advantages of the present invention will become better understood with regard to the following description, appended claims, and accompanying drawings.

BRIEF DESCRIPTION OF THE DRAWINGS

(FIG. 1B) Regional plot for the interval containing HLA-DQB1, DQA1, and DRB1. The classical HLA alleles imputed in the discovery cohort (green triangles) formed a protective haplotype DQB1*0602-DQA1*0102-DRB1*1501. (FIG. 1C) Regional plot for the second MHC interval: SNPs typed in the combined cohorts reside within the PSMB8 gene. (FIG. 1D) Regional plot for the HLA-DPB2, DPB1, and DPA1 interval. The lower panels for (FIG. 1B-D) represent linkage disequilibrium (LD) heatmaps (D') calculated based on the actual genotype data of the Beijing cohort.

(FIG. 2A) Regional association plot of the chromosome 1q32 locus; while the most strongly associated SNP resides within the CFH gene, it is a perfect proxy for CFHR1,3Δ. The lower panel represents the LD heatmap (D') calculated based on the genotype data of the Beijing cohort. (FIG. 2B) Haplotype FD analysis revealed five common haplotypes (H-1 to H-5) in the Beijing discovery cohort (freq. >0.01). The haplotype frequencies, corresponding tag-SNPs and reported disease associations are shown[22-24,36,37,41,43]. The H2 haplotype perfectly tags CFHR1,3Δ. The odds ratios (ORs) and 95% confidence intervals (95% CIs) are calculated in reference to H-1, which has an identical frequency among cases and controls. ***p=7.7×10$^{-6}$ for comparison of H-2 versus all other haplotypes. (FIG. 2C) Regional association plot of the chromosome 22 locus: the strongest association stems from the SNPs residing within HORMAD2, but the area of association spans over ~0.7 Mb region containing multiple genes.

FIG. 3. Multiplicative interaction between Chr. 22q12 (rs2412971) and Chr. 1q32 (rs6677604) loci. The allelic effects of rs2412971-A by genotype class of rs9275596 (top signal in the HLA, no interaction) and rs6677604 (top signal in at CFHR1/R3 locus on Chr. 1q32, significant interaction). The protective effect of rs2412971-A allele is reversed in homozygotes for the rs6677604-A allele, which tags a deletion in CFHR3/R1. Error bars correspond to 95% confidence intervals.

DETAILED DESCRIPTION

Figure 1A:
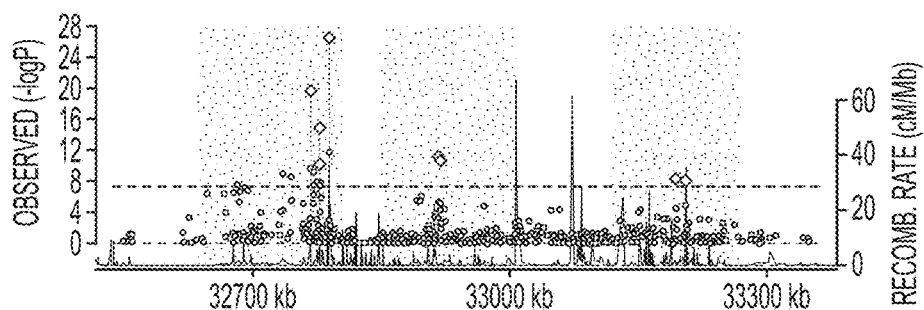
FIG. 1A-1D. High resolution view of the MHC locus. The X-axis represents physical distance (kb). The left Y-axis represent the −log(p-values) for the association statistics. The −log(p-values) in the discovery and combined cohorts are shown as blue circles and red diamonds, respectively. The right Y-axis represents the average recombination rates based on the phased HapMap haplotypes. The recombination rates are shown by the light blue line (FIG. 1A). The three intervals associated with IgA nephropathy reside within a 0.54 Mb segment on chromosome 6. The shaded areas correspond to regional plots in lower panels.

Seven protective alleles for IgA nephropathy have been discovered that can be identified by analyzing a DNA sample for seven respective SNPs. Certain embodiments of the present invention are directed to a method of identifying and treating subjects at risk of developing IgA nephropathy based on a new seven-SNP genetic risk score.

It was also discovered that certain protective alleles (rs6677604 and rs3766404) are located in a 100-kb segment on Chr. 1q31-q32.1 in intron 12 of CFH and that one allele perfectly tags a common deletion spanning the entire CFHR1 and CFHR3 genes (CFHR1,3Δ).[22,23] This protective allele confers a two-fold protection in the development of IgA nephropathy in Asian and Caucasian population (p=1×10−9). Therefore inhibiting the expression of the proteins CFHR1 or CFHR3 is the basis of a therapy for treating or preventing IgAN, since none of the subjects with these deletions had any detectable adverse side effects. Other embodiments are directed to methods of treating IgAN by administering therapeutically effective amounts of inhibitory oligonucleotides that reduce the expression of either CFHR1 or CFHR3 or both. In some embodiments microRNAs that target mRNA encoding either CFHR1 or CFHR3 or both are administered therapeutically to treat IgAN. Other embodiments are directed to screening methods to identify compounds that bind to and reduce the expression or biological activity of a either CFHR1 or CFHR3.

Summary of the Results

A genome-wide association study (GWAS) of 5,966 individuals was conducted, that identified five IgAN susceptibility loci that influence the risk of IgA nephropathy. These include 3 distinct intervals in the MHC-II region on chromosome 6p21, with the strongest signal encompassing the HLA DQB1/DQA1/DRB1 locus (abbreviated as DQB1/DRB1). Imputation of classical alleles showed that this signal was partially conveyed by a strong protective effect of the DRB1*1501-DQB1*0602 haplotype. The second signal on Chr. 6p21 encompassed a ~100 Kb region containing TAP2, TAP1, PSMB8, and PSMB9 genes (TAP2/PSMB9 locus) and the third signal on Chr. 6p21 contained the HLA DPAHDPB1/DPB2 genes (DPA1/DPB2 locus). Three protective alleles were located on Chr. 6p21 (HLA-DQB1/DRB1, PSMB9/TAP1 and DPA1/DPB2 loci), two on Chr. 1q32 (CFHR3/R1 locus) and one on Chr. 22q12 (HORMAD2 locus). Independence of these three regions on Chr. 6p21 was demonstrated by their localization within distinct LD blocks as well as genome-wide significant associations after rigorous conditional analyses. EXAMPLE 1. There was a significant association within the Complement factor H (CFH) gene cluster on Chr. 1q32, where alleles tagging a common deletion in the CFHR3 and CFHR1 genes imparted a significant protective effect (CFHR3/R1 locus). These five loci individually conferred a moderate risk of disease (OR 1.25-1.59), but together explained 4-5% of the variation in risk across the populations examined.

The GWAS study identified five minor alleles at these five loci that confer independent protection against the risk of developing IgA nephropathy (Table 2). These five protective alleles were identified by the presence of five respective independent SNPs: rs6677604 (A), rs9275596 (C), rs9357155 (A), rs1883414 (T), and rs2412971(A). In order to show that this result was not artifact, five redundant SNPs were identified corresponding to the five alleles that also had an independent protective effect on the risk of developing IgAN; these are rs3766404 (C), rs2856717 (T), rs2071543 (A), rs3129269 (T), rs2412973 (A). If a subject's DNA has any of the ten SNPs identified above, the subject has at least one protective allele that reduces the risk of developing IgAN.

A subject with no protective alleles is not necessarily at a higher than normal risk for developing IgAN, however, the presence of one or more of these protective alleles have a cumulative effect to reduce the risk of a subject developing IgAN. (Table 4.)

To follow-up the GWAS studies and better assess the risk imparted by susceptibility alleles in diverse populations, a replication study was conducted in eight independent case-control cohorts of Asian, European and African-American ancestry (N=4,789), followed by meta-analysis with risk-score modeling in 12 cohorts (N=10,755), and geospatial analysis in 85 world populations. Four susceptibility loci were robustly replicated and all five loci showed genome-wide significance in the combined cohort (P=$5\times10^{-32}$–$3\times10^{-10}$), with heterogeneity detected only at the PSMB9/TAP1 locus ($I^2$=0.60). Two new independent risk alleles were identified within the HLA-DQB1/DRB1 locus, rs9275224 (A) and rs2856717 (T), defining multiple risk and protective haplotypes within this interval. A new genetic interaction between loci on Chr.1p36 and Chr.22q22 was also discovered. Example 2.

Between the two studies a total of seven loci harboring seven independent protective alleles and 12 corresponding SNPs were identified. These seven independent protective alleles can be identified by the presence of seven respective independent SNPs: (i) rs6677604 (A), rs9275596 (C), rs9357155 (A), rs1883414 (T), rs2412971(A), rs9275224 (A) and rs2856717 (T); or (ii) rs3766404 (C), rs2856717 (T), rs2071543 (A), rs3129269 (T), rs2412973 (A), rs9275224 (A) and rs2856717 (T). [rs6677604 (A), rs3766404 (C)], [rs9357155 (A), rs2071543 (A)], [rs1883414 (T), rs3129269 (T)] and [rs2412971(A), rs2412973 (A)].

In the embodiments of the invention it can be determined whether a subject has a protective allele for IgAN by analyzing the subject's DNA for any or preferably all of the seven IgAN protective alleles.

A stepwise regression algorithm in the entire cohort defined a new risk score that retained the 7 SNPs exhibiting an independent protective effect on IgAN: rs6677604 (A), rs9275224 (A), rs2856717 (T), rs9275596 (C), rs9357155 (A), rs1883414 (T) and rs2412971 (A). Some embodiments are directed to computing a subject's genetic risk score based on the weighted sum of the number of protected alleles at each locus, multiplied by the log of the odds ratio for each of the individual loci. A genetic risk score can also be based on the redundant SNPs identified in the first GWAS study for five of the seven protective alleles, rs3766404 (C), rs2856717 (T), rs2071543 (A), rs3129269 (T), rs2412973 (A), and the two alleles identified in the second larger study: rs9275224 (A) and rs2856717 (T).

Another set of embodiments are directed to microarrays of bound oligonucleotide probes that are complementary to and specifically hybridize to any or all of the twelve SNPs to screen a patient's DNA for one or more IgAN protective alleles. In an embodiment the array is designed to detect seven SNPS that represent seven independent protective alleles. In this list the SNPs in brackets are redundant. A screen can include either SNP to indicate the protective allele: [rs6677604 (A), rs3766404 (C)], rs9275596 (C), rs9275224, rs2856717 [rs9357155 (A), rs2071543 (A)], [rs1883414 (T), rs3129269 (T)] and [rs2412971(A), rs2412973 (A)].

A set of embodiments are directed to a method for determining if a subject has a reduced risk of the developing IgAN due to the presence of one or more protective alleles.

Knowing the genetic risk for developing IgAN is also important, for example in determining whether to begin treatment of a subject that has symptoms of the disease such as blood or protein or both in the urine and/or reduced kidney function. If the subject has a reduced genetic risk of developing IgAN because one or more protective alleles are detected in a DNA sample, then it is not necessary to begin drug therapy. However, if the subject has an increased genetic risk of developing IgAN due to the absence of at least one protective allele, then drug therapy should be initiated. The typical therapy for treating IgAN with therapeutically effective amounts of one or more steroids.

A set of embodiments is directed to methods for determining a genetic risk score for a subject by calculating the weighted sum of the number of protected alleles at each locus, multiplied by the log of the odds ratio for each of the individual loci. If a subject is prone to blood or protein in the urine or reduced kidney function, a physician may want to test the patient for the risk of developing IgAN.

Certain additional embodiments of the invention are based in part on the discovery that certain protective alleles (rs6677604 and rs3766404) are located in a 100-kb segment on Chr. 1q31-q32.1 in intron 12 of CFH that contains complement factor H (CFH) and the related CFHR3, CFHR1, CFHR4, CHFR2, CFHR5 genes. It was discovered that this segment encompasses an allele that perfectly tags a common deletion spanning the entire CFHR1 and CFHR3 genes (CFHR1,3Δ)[22,23]. This protective allele confers a two-fold protection in the development of IgA nephropathy in Asian and Caucasian population (p=$1\times10$–9). It has been discovered that inhibiting the expression of the proteins CFHR1 or CFHR3 is the basis of a new therapy for treating or preventing IgAN, since none of the subjects with these deletions had any detectable adverse side effects.

Another set of embodiments are directed to methods for treating or preventing IgAN by reducing the expression or biological activity of CFHR1 or CFHR3 or both in a subject by administering therapeutically effective amounts of inhibitory oligonucleotides, either systemically or possibly locally to the kidney, or administrating an antibody or a small chemical inhibitor that inhibit the proteins.

The gene, cDNA and mRNA sequences for CHFR1 and CHFR3 are known and available publicly. It is routine to design inhibitory oligonucleotides based on this sequence information. FHR-1 gene is also known as CHFR1, CFHL1, CFHL, FHR1 and HFL1. The reference form of human HFR-1 cDNA (see Estaller et al., 1991, J. Immunol. 146: 3190-3196) and genomic sequences have been determined. encodes a polypeptide 330 amino acids in length having a predicted molecular weight of 39 kDa. cDNA and amino acid sequence data for human FHR-1 are found in the EMBL/GenBank Data Libraries under accession number M65292. The FHR-1 gene sequence is found under GenBank accession number AL049741. *Homo sapiens* complement factor H-related 1 (CFHR1), mRNA is publically available as Ref Seq Summary (NM_002113): This gene encodes a secreted protein belonging to the complement factor H protein family. Genomic Size: 12459.

The FHR-3 gene is also known as CFHR3, CFHL3, FHR3 and HLF4. The reference form of human HFR-3 cDNA (see Strausberg et al., Proc. Natl. Acad. Sci USA 99:16899-16903) and genomic sequences have been determined. The FHR-3 cDNA encodes a polypeptide 330 amino acids in length having a predicted molecular weight of 38 kDa. cDNA and amino acid sequence data for human FHR-3 are found in the EMBL/GenBank Data Libraries under accession number BC058009. The FHR-3 gene sequence is found under GenBank accession number AL049741. CHFR3 Accession Number, NM_021023.

Other protective alleles have been discovered that provide a two-fold reduction in the risk of developing IgAN. One locus is tagged by SNP rs9357155 that lies in a ~100 kb segment of LD and lies 128 kb centromeric to rs9275596 in the second independent interval at 6p21 and contains TAP2, TAP1, PSMB8, and PSMB9, interferon-regulated genes that have been implicated in antigen generation and processing for presentation by MHC I molecules; they also play an important role in modulation of cytokine production and cytotoxic T-cell response. PSMB8 expression is increased in PBMCs from IgAN subjects.[35]. To our knowledge, this locus has not been identified in any prior GWAS. It has been discovered that the supporting SNP rs2071543 (also on chromosome 6) is a missense variant in PSMB8 (Q49K) that is at a position which is completely conserved among all orthologs.

As described above, the methods are also useful in genetic confirmations of a diagnosis of IgAN, or to determine a therapeutic regimen for a subject.

Certain other embodiments, described in detail below, are directed to methods for identifying compounds such as small molecules, peptides, antibodies or fragments thereof that bind to a target protein CFHR1 or CFHR 3, or a biologically active fragment or variant thereof, thereby reducing the biological activity of the protein. Such inhibitory compounds have potential therapeutic utility in treating IgAN in a subject.

Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

"Allele": A particular form of a genetic locus, distinguished from other forms by its particular nucleotide sequence, or one of the alternative polymorphisms found at a polymorphic site.

"Correlation": A correlation between a phenotypic trait and the presence or absence of a genetic marker (or haplotype or genotype) can be observed by measuring the phenotypic trait and comparing it to data showing the presence or absence of one or more genetic markers. Some correlations are stronger than others, meaning that in some instances subjects will display a particular genetic marker (i.e., 100% correlation. In the present application, a haplotype which contains information relating to the presence or absence of multiple markers is correlated to a genetic predisposition to develop IgAN.

"Genetic predisposition": Susceptibility of a subject to a disease, such as IgAN. Detecting a genetic predisposition includes detecting the risk of developing the disease, and determining the susceptibility of that subject to developing the disease or to having a poor prognosis for the disease. Thus, if a subject has a genetic predisposition to a disease they do not necessarily develop the disease but are at a higher than normal risk for developing the disease.

"Gene": A segment of DNA that contains the coding sequence for a protein, wherein the segment may include promoters, exons, introns, and other untranslated regions that control expression.

"Genotype": A genotype is the genetic makeup of a cell, an organism, or an individual (i.e. the specific allele makeup of the individual) usually with reference to a specific character under consideration.

"Protective allele" means an allele that confers a lower risk of developing IgA nephropathy.

"Haplotype": is a combination of alleles (DNA sequences) at adjacent locations (loci) on the chromosome that are transmitted together. A haplotype may be one locus, several loci, or an entire chromosome depending on the number of recombination events that have occurred between a given set of loci.

"Linkage": The association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set.

"Linkage Disequilibrium (LD)": Co-occurrence of two genetic loci (e.g., markers) at a frequency greater than expected for independent loci based on the allele frequencies. Linkage disequilibrium (LD) typically occurs when two loci are located close together on the same chromosome. When alleles of two genetic loci (such as a marker locus and a causal locus) are in strong LD, the allele observed at one locus (such as a marker locus) is predictive of the allele found at the other locus (for example, a causal locus contributing to a phenotypic trait).

"Locus": A location on a chromosome or DNA molecule corresponding to a gene or a physical or phenotypic feature, where physical features include polymorphic sites.

"Mutation": Any change of a nucleic acid sequence as a source of genetic variation.

"Odds Ratio": A calculation performed by analysis of a two by two contingency table. In one example, the first column provides a risk indicator in the absence of a disease (e.g., IgAN). The second column provides the same risk indicator in the presence of the same disease. The first row lists the risk indicator in the absence of a risk factor (such as race) and the second row lists the same risk indicator in the presence of the same risk factor (i.e., race). The Odds Ratio (OR) is determined as the product of the two diagonal entries in the contingency table divided by the product of the two off-diagonal entries of the contingency table. An OR of 1 is indicative of no association. Accordingly, very large or very small ORs are indicative of a strong association between the factors under investigation. The OR is independent of the ratio of cases or controls in a study, group or subset.

"Polymorphism": A variation in a gene sequence. Polymorphisms can be referred to, for instance, by the nucleotide position at which the variation exists, by the change in amino acid sequence caused by the nucleotide variation, or by a change in some other characteristic of the nucleic acid molecule or protein that is linked to the variation. In the instant application "polymorphism" refers a traditional definition meaning that the minor allele frequency must be greater than at least 1%.

A "single nucleotide polymorphism (SNP)" is a single base (nucleotide) polymorphism in a DNA sequence among individuals in a population. SNP genotyping is the measurement of genetic variations of single nucleotide polymorphisms (SNPs) between members of a species. SNPs are one of the most common types of genetic variation. An SNP is a single base pair mutation at a specific locus, usually consisting of two alleles (where the rare allele frequency is >1%). SNPs are involved in the etiology of many human diseases.

A "tag SNP" is a SNP that by itself or in combination with additional Tag SNPs indicates the presence of a specific haplotype, or of one member of a group of haplotypes. The haplotype or haplotypes can indicate a genetic factor is associated with risk for disease, thus a tag SNP or combination of tag SNPs indicates the presence or absence of risk factors for disease. A "tag SNP" is a representative single nucleotide polymorphism (SNP) in a region of the genome with high linkage disequilibrium (the non-random association of alleles at two or more loci) that is associated with a disease, such as IgAN. A tag SNP can be used to identify other SNPs, such as those with a specified $r^2$ value from the tag SNP, which are associated with the disease.

"IgA Nephropathy (IgAN"): A disorder that specifically leads to damage of the kidneys that is normally diagnosed by kidney biopsy showing predominant deposition Immunoglobulin A on immunofluorescence coupled with light microscopy showing mesangial proliferation, or expansion IGs include IgA nephropathy. IgAN can be chronic or acute. IgA nephropathy (also known as IgA nephritis, IgAN, Berger's disease and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus.

"Risk Allele": A "risk" allele is an allele associated with a particular type or form of disease. The risk allele identifies a tag single nucleotide polymorphism that can be used to detect or determine the risk for a disease, such as IgAN.

"Sample": means a biological sample obtained from a subject. For embodiments of the present invention of diagnostic tests for predisposition to IgA, a blood sample such as whole blood or serum is preferred. However any biological sample can be used, including, but not limited to, cells, tissues, and bodily fluids, such as: blood; derivatives and fractions of blood, such as serum; biopsied or surgically removed tissue, urine; sputum; cerebrospinal fluid or bone marrow aspirates.

"Subject" shall mean any organism including, without limitation, a mammal such as a mouse, a rat, a dog, a guinea pig, a ferret, a rabbit and a primate. In the preferred embodiment, the subject is a human being.

"Therapeutically effective amount": An amount of a therapeutic agent that alone, or together with one or more additional therapeutic agents, induces the desired response, such as decreasing the risk of developing IgAN or decreasing the signs and symptoms of IgAN. "Reference Allele": A genotype that predominates in a natural population of organisms that do not have a disease process. The reference genotype differs from mutant forms. Unless otherwise explained, all technical and scientific terms used herein have the same meaning as commonly understood by one of ordinary skill in the art to which this disclosure belongs.

Nucleic Acids

Methods of isolating and analyzing nucleic acid molecules from a biological sample are routine, for example using PCR to amplify the molecules from the sample, or by using a commercially available kit to isolate DNA. Nucleic acid molecules isolated from a biological sample can be amplified using routine methods to form nucleic acid amplification products.

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

Amplification of nucleic acid molecules: Optionally, the nucleic acid samples obtained from the subject are amplified prior to detection. Target nucleic acids are amplified to obtain amplification products, including sequences from a tag SNP, can be amplified from the sample prior to detection. Typically, DNA sequences are amplified, although in some instances RNA sequences can be amplified or converted into cDNA, such as by using RT PCR.

Methods for labeling nucleic acid molecules so they can be detected are well known. Examples of such labels include non-radiolabels and radiolabels. Non-radiolabels include, but are not limited to an enzyme, chemiluminescent compound, fluorescent compound (such as FITC, Cy3, and Cy5), metal complex, hapten, enzyme, colorimetric agent, a dye, or combinations thereof. Radiolabels include, but are not limited to, $^{125}$I, $^{32}$P and $^{35}$S. For example, radioactive and fluorescent labeling methods, as well as other methods known in the art, are suitable for use with the present disclosure. In one example, primers used to amplify the subject's nucleic acids are labeled (such as with biotin, a radiolabel, or a fluorophore). In another example, amplified target nucleic acid samples are end-labeled to form labeled amplified material. For example, amplified nucleic acid molecules can be labeled by including labeled nucleotides in the amplification reactions.

Nucleic acid molecules corresponding to one or more tag SNPs or haplotype blocks including the tag SNP can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Hybridization conditions for a given combination of array and target material can be optimized using methods known to one of skill in the art (see U.S. Pat. No. 5,981,185). Once the target nucleic acid molecules have been hybridized with the labeled probes, the presence of the hybridization complex can be analyzed, for example by detecting the complexes. Methods for detecting hybridized nucleic acid complexes are well known in the art.

"Allele Specific PCR": Allele-specific PCR differentiates between target regions differing in the presence of absence of a variation or polymorphism. PCR amplification primers are chosen based upon their complementarity to the target sequence, such as nucleic acid sequence in a haplotype block including a tag SNP, a specified region of an allele including a tag SNP, or to the tag SNP itself. The primers bind only to certain alleles of the target sequence. This method is described by Gibbs, Nucleic Acid Res. 17:12427 2448, 1989, herein incorporated by reference.

"Allele Specific Oligonucleotide Screening Methods": Further screening methods employ the allele-specific oligonucleotide (ASO) screening methods (e.g. see Saiki et al., Nature 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the reference allele (haplotype block).

"Ligase Mediated Allele Detection Method": Ligase can also be used to detect point mutations, such as the tag SNPs disclosed herein, in a ligation amplification reaction (e.g. as described in Wu et al., Genomics 4:560-569, 1989). The ligation amplification reaction (LAR) utilizes amplification of specific DNA sequence using sequential rounds of template dependent ligation (e.g. as described in Wu, supra, and Barany, Proc. Nat. Acad. Sci. 88:189-193, 1990).

"Denaturing Gradient Gel Electrophoresis": Amplification products generated using the polymerase chain reaction can be analyzed by the use of denaturing gradient gel electrophoresis. Different alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

"Non-gel Systems": Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

"Non-PCR Based Allele detection": The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}P$ or $^{35}S$. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Nucleic Acid Arrays

Certain embodiments are directed to a microarrays for detecting one or more protective alleles in a DNA sample, which alleles indicate a genetic predisposition to IgAN in a human subject. The array contains probes complementary to at least one single nucleotide polymorphism indicating an independent protective allele, preferably probes are included for hybridizing all seven independent protective alleles. Each of the single nucleotide polymorphisms is associated with a specific protective allele for IgAN and is complementary to the targeted SNP.

It will be readily apparent to one skilled in the art that the exact formulation of probes on an array is not critical as long as the user is able to select probes for inclusion on the array that fulfill the function of hybridizing to the targeted SNPs. The array can be modified to suit the needs of the user. Thus, analysis of the array can provide the user with information regarding the number and/or presence of protective alleles in a given sample. The hybridization of a probe complementary to a protective allele in an array can indicate that the subject from whom the sample was derived is at an elevated risk for developing a disease such as IgAN; or alternatively if it hybridizes to a protective allele the subject has a reduced risk.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mm (0.001 inch) to about 20 mm although the thickness of the film is not critical and can be varied over a fairly broad range. Biaxially oriented polypropylene (BOPP) films are also suitable in this regard; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., Anal. Biochem. 217:306-10, 1994. In one example, the oligonucleotides are synthesized onto the support using conventional chemical techniques for preparing oligonucleotides on solid supports (see PCT Publication No. WO 85/01051 and PCT Publication No. WO 89/10977, or U.S. Pat. No. 5,554, 501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90.degree. to permit synthesis to proceed within a second (2degrees) set of rows that are now perpendicular to the first set. This process creates a multiple-channel array whose intersection generates a plurality of discrete cells. In particular examples, the oligonucleotide probes on the array include one or more labels, which permit detection of oligonucleotide probe:target sequence hybridization complexes.

Kits

Certain embodiments are directed to kits that can be used to detect SNPs indicating the presence of one or more protective alleles for IgAN in a DNA sample. The disclosed kits include a binding molecule, such as an oligonucleotide probe that selectively hybridizes to an allele of a haplotype block including a particular known SNP. Alternatively or additionally, the kits can include one or more isolated primers or primer pairs for amplifying a target nucleic acid, such as a haplotype including a SNP. For example, the kit can include primers for amplifying a haplotype including one, two, three, four, five, six, seven, eight, nine, ten SNPs associated with a particular protective allele.

The kit can further include one or more of a buffer solution, a conjugating solution for developing the signal of interest, or a detection reagent for detecting the signal of interest, each in separate packaging, such as a container. In another example, the kit includes a plurality of size-associated marker target nucleic acid sequences for hybridization with a detection array. The target nucleic acid sequences can include oligonucleotides such as DNA, RNA, and peptide-nucleic acid, or can include PCR fragments. The kit can also include instructions in a tangible form, such as written instructions or in a computer-readable format.

Inhibitory Oligonucleotides

Other embodiments of the present invention are directed to the use of inhibitory oligonucleotides such as antisense DNA or RNA (or chimeras thereof), small interfering RNA (siRNA), micro RNA (miRNA), short hairpin RNA, ribozymes, supermir, and aptamers, to reduce or inhibit expression of CFHR1 and CFHR 3, hereafter "the targeted proteins." The mRNA and gene sequences encoding the targeted proteins are set forth herein by accession numbers. Based on these known sequences, inhibitory oligonucleotides that hybridize sufficiently to the respective gene or mRNA encoding the targeted proteins to turn off expression can be readily designed and engineered using methods known in the art.

Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans. See for example Agrawal, S. and Zhao, Q. (1998) Curr. Opi. Chemical Biol. Vol. 2, 519-528; Agrawal, S and Zhang, R. (1997) CIBA Found. Symp. Vol. 209, 60-78; and Zhao, Q, et al., (1998), Antisense Nucleic Acid Drug Dev. Vol 8, 451-458; the entire contents of which are hereby incorporated by reference as if fully set forth herein. Anderson, K. O., et al., (1996) Antimicrobial Agents Chemother. Vol. 40, 2004-2011, and U.S. Pat. No. 6,828,151 by Borchers, et al.

The oligonucleotides used herein are synthesized in vitro and do not include compositions of biological origin. Based on these known sequences of the targets (genes or mRNA) therapeutic oligonucleotides can be engineered using methods known in the art. Different combinations of these therapeutic agents can be formulated for administration to a subject using methods well known in the art.

These nucleic acids act via a variety of mechanisms. siRNA or miRNA can down-regulate intracellular levels of specific proteins through a process termed RNA interference (RNAi). Following introduction of siRNA or miRNA into the cell cytoplasm, these double-stranded RNA constructs can bind to a protein termed RISC. RNA-Induced Silencing Complex, or RISC, is a multiprotein complex that incorporates one strand of a small interfering RNA (siRNA) or micro RNA (miRNA). RISC uses the siRNA or miRNA as a template for recognizing complementary mRNA. When it finds a complementary strand, it activates RNase and cleaves the RNA. This process is important both in gene regulation by microRNAs and in defense against viral infections, which often use double-stranded RNA as an infectious vector RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against mRNA encoding a target protein. To date, siRNA constructs have shown the ability to specifically down-regulate target proteins in both in vitro and in vivo models and they are currently being evaluated in clinical studies.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA. Advanced human clinical assessments of several antisense drugs are currently underway.

It is desirable to optimize the stability of the phosphodiester internucleotide linkage and minimize its susceptibility to exonucleases and endonucleases in serum. (Zelphati, O., et al., Antisense. Res. Dev. 3:323-338 (1993); and Thierry, A. R., et al., pp 147-161 in Gene Regulation: Biology of Antisense RNA and DNA (Eds. Erickson, R P and Izant, J G; Raven Press, NY (1992)).

Therapeutic nucleic acids being currently being developed do not typically employ the basic phosphodiester chemistry found in natural nucleic acids, because of these and other known problems. Modifications have been made at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130).

Nucleic acids for use in embodiments of the present invention may be of various lengths, generally dependent upon the particular form of nucleic acid, typically from about 10 to 100 nucleotides in length. In various related embodiments, oligonucleotides, single-stranded, double-stranded, and triple-stranded, may range in length from about 10 to about 50 nucleotides, from about 20 o about 50 nucleotides, from about 15 to about 30 nucleotides, from about 20 to about 30 nucleotides in length.

In particular embodiments, the oligonucleotide (or a strand thereof) specifically hybridizes to or is complementary to a target polynucleotide, preferably an mRNA molecule. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression of the target, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions, e.g. mismatches, as compared to the region of a gene or mRNA sequence that it is targeting or to which it specifically hybridizes.

Small interfering RNA (siRNA) has essentially replaced antisense ODN and ribozymes as the next generation of targeted oligonucleotide drugs under development. SiRNAs are RNA duplexes normally 16-30 nucleotides long that can associate with a cytoplasmic multi-protein complex known as RNAi-induced silencing complex (RISC). RISC loaded with siRNA mediates the degradation of homologous mRNA transcripts; therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., Nature Reviews 6:443-453 (2007).

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S, and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded oligonucleotides comprising two separate strands, i.e. a sense strand and an antisense strand, e.g., small interfering RNA (siRNA); double-stranded oligonucleotide comprising two separate strands that are linked together by non-nucleotidyl linker; oligonucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule.

A single strand siRNA compound may be sufficiently long that it can enter the RISC and participate in RISC mediated cleavage of a target mRNA. A single strand siRNA compound is typically at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

A "double stranded siRNA compound" as used herein, is a siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. As used herein, term "antisense strand" means the strand of a siRNA compound that is sufficiently complementary to a target molecule, e.g. a target RNA.

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. The double strand portion of a double stranded siRNA compound may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the siRNA compound is sufficiently large that it can be cleaved by an endogenous molecule, e.g., by Dicer, to produce smaller siRNA compounds, e.g., siRNAs agents The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of a siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also within the invention.

The siRNA compounds described herein, including double-stranded siRNA compounds and single-stranded siRNA compounds can mediate silencing of a target RNA, e.g., mRNA, e.g., an mRNA transcript of a gene that encodes a protein. A gene may also be targeted. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA compound of 21 to 23 nucleotides.

MicroRNAs

Micro RNAs (miRNAs) are a highly conserved class of small RNA molecules that are transcribed from DNA in the genomes of plants and animals, but are not translated into protein. Processed miRNAs are single stranded (about 17-25 nucleotide (nt)) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

Antisense Oligonucleotides: In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA. Antisense oligonucleotides are thought to inhibit gene expression by binding to a complementary mRNA. Binding to the target mRNA can lead to inhibition of gene expression either by preventing translation of complementary mRNA strands by binding to it or by leading to degradation of the target mRNA Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. See for example (U.S. Pat. Nos. 5,739,119 and 5,759,829); (Jaskulski et al., Science. 1988 Jun. 10; 240 (4858):1544-6; Vasanthakumar and Ahmed, Cancer Commun. 1989; 1(4):225-32; Penis et al., Brain Res Mol Brain Res. 1998 Jun. 15; 57(2):310-20; U.S. Pat. Nos. 5,801,154; 5,789,573; 5,718,709 and 5,610,288); (U.S. Pat. Nos. 5,747, 470; 5,591,317 and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Aptamers: Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers may be RNA or DNA based, and may include a riboswitch. Regulatory elements are known as riboswitches and are defined as mRNA elements that bind metabolites or metal ions as ligands and regulate mRNA expression by forming alternative structures in response to this ligand binding (Nudler & Mironov 2004; Tucker & Breaker 2005; Winkler 2005). Although they can bind proteins like antibodies, aptamers are not immunogenic, even at doses up to 1000 times the therapeutic dose in primates.

A riboswitch is a part of an mRNA molecule that can directly bind a small target molecule, and whose binding of the target enables it to regulate its own activity, depending on the presence or absence of its target molecule. Riboswitches are most often located in the 5' untranslated region (5' UTR; a stretch of RNA that precedes the translation start site) of bacterial mRNA. There they regulate the occlusion of signals for transcription attenuation or translation initiation. Edwards, A. L. et al., (2010) Riboswitches: A Common RNA Regulatory Element. Nature Education3(9):9.

Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Ribozymes: According to another embodiment of the invention, targeted mRNA is inhibited by ribozymes, which have specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis delta virus, group I intron or RNaseP RNA (in association with an RNA guide sequence) or Neurospora VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Ribozyme constructs need not be limited to specific motifs mentioned herein. Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, and synthesized to be tested in vitro and in vivo, as described therein. Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Supermir: A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. This term includes oligonucleotides composed of naturally-occurring nucleobases, sugars and covalent internucleoside (backbone) linkages and which contain at least one non-naturally-occurring portion which functions similarly. Such modified or substituted oligonucleotides are preferred over native forms because of desirable properties such as, for example, enhanced cellular uptake, enhanced affinity for nucleic acid target and increased stability in the presence of nucleases. In a preferred embodiment, the supermir does not include a sense strand, and in another preferred embodiment, the supermir does not self-hybridize to a significant extent. A supermir can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or n nucleotides, e.g., 5 nucleotides. The duplexed region can be connected by a linker, e.g., a nucleotide linker, e.g., 3, 4, 5, or 6 dTs, e.g., modified dTs. The supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Oligonucleotide Modifications: Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications of oligonucleotides can confer improved properties, and, e.g., can render oligonucleotides more stable to nucleases.

As oligonucleotides are polymers of subunits or monomers, many of the modifications described below occur at a position which is repeated within an oligonucleotide, e.g., a modification of a base, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal region, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of a double-stranded oligonucleotide or may only occur in a single strand region of a double-stranded oligonucleotide. E.g., a phosphorothioate modification at a non-bridging oxygen position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g., different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications to oligonucleotides that come within the scope of the invention include modifications to the Phosphate Group for example to increase resistance of the oligoribonucleotide to nucleolytic breakdown, or Replacement of the Phosphate Group by non-phosphorus containing connectors, or Replacement of Ribophosphate Backbone wherein the phosphate linker and ribose sugar are replaced by nuclease resistant nucleoside or nucleotide surrogates. or Sugar Modifications of all or some of the sugar groups of the ribonucleic acid. E.g., the 2' hydroxyl group (OH) can be modified or replaced with a number of different "oxy" or "deoxy" substituents to enhance stability.

Screening for Compounds Bind to and Inhibit CFHR1 and CFHR 3

A set of embodiments are directed to methods for identifying compounds (herein also ligands) such as small molecules, peptides, antibodies or fragments thereof that bind to a target protein that is either CFHR1 or CFHR 3, or a biologically active fragment or variant thereof, thereby reducing the biological activity of the protein. Such inhibitory compounds have potential therapeutic utility in treating IgAN in a subject.

In some embodiments the compound is selected from a library of compounds including small molecules or peptides, carbohydrates, organic molecules or antibodies. The compound can be selected from a combinatorial library of compounds.

In some embodiments the compounds are optionally bound to a solid support, preferably an array wherein the location and identity of the compound are known, and the target protein is labeled for easy detection. The binding of the compound to the target can be either non-covalent interaction or covalent. Non-covalent binding refers to an association that may be disrupted by methods well known to those skilled in the art, such as the addition of an appropriate solvent, or a change in ionic conditions. Conversely, when a covalent linkage is formed the protein will not be released from the compound by ionic conditions and solvents that would disrupt non-covalent binding.

A "compound" as defined herein is an entity which has an intrinsic binding affinity for the target (CHFR1 or CHFR3). The compound can be a molecule, or a portion of a molecule which binds the target. The compounds are typically small organic molecules, but may also be other sequence-specific binding molecules, such as peptides (D-, L- or a mixture of D- and L-), peptidomimetics, complex carbohydrates or other oligomers of individual units or monomers which bind specifically to the target. The term also includes various derivatives and modifications that are introduced in order to enhance binding to the target. Compounds that inhibit a biological activity of a target molecule are called "inhibitors" of the target "Small molecules" are usually less than about 10 kDa molecular weight, and include but are not limited to synthetic organic or inorganic compounds, peptides, (poly) nucleotides, (oligo)saccharides and the like. Small molecules specifically include small non-polymeric (i.e. not peptide or polypeptide) organic and inorganic molecules. Many pharmaceutical companies have extensive libraries of such molecules, which can be conveniently screened by using the against the target proteins. Preferred small molecules have molecular weights of less than about 1000 Da, more preferably about 500 Da, and most preferably about 250 Da.

The phrase "adjusting the conditions" as used herein refers to subjecting a target protein, to any individual, combination or series of reaction conditions or reagents necessary to cause a covalent bond to form between the compound and the target.

"Functional variants" of a molecule herein are variants having an activity in common with the reference molecule "Active" or "activity" means a qualitative biological property of the targeted protein. Biological property is not limiting.

Direct, non-competitive binding assays are advantageously used to screen libraries of compounds for those that selectively bind to a preselected target. Binding is detected using any physical method that measures the altered physical property of the compound bound to the target protein. The structure of the bound compound can also be determined. The methods used will depend, in part, on the nature of the library screened. The methods of the present invention provide a simple, sensitive assay for high-throughput screening of libraries of compounds to identify compounds that inhibit or reduce the biological activity of the target protein.

As used herein, a "library" refers to a plurality of compounds with which a target protein molecule is contacted. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, a "label" or "detectable label" is a composition that is detectable, either directly or indirectly, by spectroscopic, photochemical, biochemical, immunochemical, or chemical means.

Methods are described in which a preselected target protein having a detectable label is used to screen a library of compounds. The methods can also be adapted to put the label on the compound. Any complexes formed between the target and a member of the library are identified using methods that detect the labeled target bound to a compound/test compound. In an embodiment compounds are bound to a solid support such as a bead. Binding can also be assayed in solution where the compounds are not bound to a support. Bound complexes can be separated from the unbound target in the liquid phase by a known means such as, but not limited to, flow cytometry, affinity chromatography, manual batch mode separation, suspension of beads in electric fields, and microwave. The detectably labeled complex can then be identified by the label on the target protein and removed from the uncomplexed, unlabeled compounds in the library.

Where a solid support is used, the method for identifying a test compound that binds to a target includes (a) contacting a detectably labeled target molecule with a library of solid support-attached compounds under conditions that permit direct binding of the labeled target to a member of the library of solid support-attached compounds so that a detectably labeled target target:support-attached test compound complex is formed; (b) separating the detectably labeled target:support-attached test compound complex formed in step (a) from uncomplexed target molecules and compounds; and optionally (c) determining a structure of the test compound of the RNA support-attached test compound complex.

The compound that binds to the target can then be tested in a biological assay (in vitro or cell based or chemical) to determine if it reduces the biological activity of the target. Detectable labels include a fluorescent dye, phosphorescent dye, ultraviolet dye, infrared dye, visible radiolabel, enzyme, spectroscopic colorimetric label, affinity tag, or nanoparticle.

Libraries of Small Molecules

Libraries screened using the methods of the present invention can comprise a variety of types of compounds. In all of the embodiments described below, all of the libraries can be optionally synthesized on solid supports or the compounds of the library can be attached to solid supports by linkers.

In some embodiments, the compounds are peptide molecules. In a non-limiting example, peptide molecules can exist in a phage display library. In other embodiments, types of compounds include, but are not limited to, peptide analogs including peptides comprising non-naturally occurring amino acids, e.g., D-amino acids, phosphorous analogs of amino acids, such as .alpha.-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used. In a preferred embodiment, the combinatorial libraries are small organic molecule libraries, such as, but not limited to, benzodiazepines, isoprenoids, thiazolidinones, metathiazanones, pyrrolidines, morpholino compounds, and diazepindiones. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., Advanced ChemTech Europe Ltd., Cambridgeshire, UK; ASINEX, Moscow Russia; BioFocus plc, Sittingbourne, UK; Bionet Research (A division of Key Organics Limited), Camelford, UK; ChemBridge Corporation, San Diego, Calif.; ChemDiv Inc., San Diego, Calif.; ChemRx Advanced Technologies, South San Francisco, Calif.; ComGenex Inc., Budapest, Hungary; Evotec OAI Ltd, Abingdon, UK; IF LAB Ltd., Kiev, Ukraine; Maybridge plc, Cornwall, UK; PharmaCore, Inc., North. Carolina; SIDDCO Inc, Tucson, Ariz.; TimTec Inc, Newark, Del.; Tripos Receptor Research Ltd, Bude, UK; Toslab, Ekaterinburg, Russia).

In one embodiment, the combinatorial compound library for the methods of the present invention may be synthesized. Combinatorial compound libraries useful for the methods of the present invention can be synthesized on solid supports. As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, doped polystyrene beads (as described by Fenniri et al., 2000, J. Am. Chem. Soc. 123:8151-8152), alumina gels, and polysaccharides. A suitable solid support may be selected on the basis of desired end use and suitability for various synthetic protocols. In some embodiments of the present invention, compounds can be attached to solid supports via linkers Screening comprises contacting a labeled target protein with an individual, or small group, of the components of the compound library, or with a large number of compounds bound on an array. Preferably, the contacting occurs in an aqueous solution, and most preferably, under physiologic conditions. The aqueous solution preferably stabilizes the labeled target nucleic acid and prevents denaturation or degradation of the nucleic acid without interfering with binding of the compounds.

Generally, it is convenient to test the libraries using a one well-one compound approach to identify compounds which compete with the peptide fusion protein or high affinity peptide for binding to the receptor. A single compound per well can be used, at about 1 microM each or at any convenient concentration depending on the affinity of the receptor for the compounds and the peptide against which they are being tested. Compounds may be pooled for testing, however this approach requires deconvalution. Gilchrist, U.S. Pat. No. 7,294,472.

Assays to Test CFHR1 and CFHR3 Activity

Any assay for determining the biological activity of the targeted proteins. One such assay is a hemolysis assay. CFHR3, CFHR1 will be added to CFHR3/CFHR1-depleted plasma (30%) or to serum derived from patients with deletions of the CFHR1 and CHFR3 genes. Serum will be incubated at 37° C. for 20 min with about 2×107 sheep erythrocytes in activation buffer C (20 mm Hepes, 144 mm NaCl, 7 mm MgCl2, 10 mm EGTA, pH 7.4). Supernatants will be recorded at 415 nm. Generation of complement activation products C3a and C5a will be followed by ELISA. Increasing amounts of CFHR3 (0.02-1 μm), CFHR1 (0.02-1.16 μm), will added to CFHR1- and CFHR3-deficient plasma from a healthy donor (20%) and incubated for 20 min at 37° C. with chicken erythrocytes (5×106) which are more sensitive to hemolysis than sheep erythrocytes. Supernatants will be recorded at 415 nm. These assays will be repeated in the presence of inhibitory compounds to test their activity and specificity in inhibiting CFHR3, CFHR1, or factor H activity.

In inhibition of the ability of CFHR1 and CFHR3 and CFH to regulate C3 convertase by a candidate compound in a screen involves generating C3 convertase by incubation of C3b (5 μg/ml) and C3 (50 μg/ml) with factor D (2.5 μg/ml), properdin (2.5 μg/ml) and factor B (5 μg/ml) in activation buffer C (20 mm Hepes, 144 mm NaCl, 7 mm MgCl2, 2 mm NiCl2, 10 mm EGTA, pH 7.4). Activity of C3 convertase will be measured by C3a generation after incubation of constant amounts of C3 (50 μg/ml) and increasing concentrations of CFHR1, CFHR3 (25 and 50 μg/ml, 0.5 and 1 μm). C3a concentrations can be determined by ELISA (Quidel, USA). For the determination of C3 cleavage in plasma, ΔCFHR3/CFHR1 plasma (10%) will be incubated with 20 or 40 μg/ml of CFHR3 (0.4 or 0.8 μm), CFHR1 (0.46 or 0.93 μm), factor H or BSA in complement activation buffer C. C3a generation was followed by western blot analysis. In competition assays, C3b (5 μg/ml) will be immobilized to the surface of a microtiter plate (nunc maxisorb) and incubated with increasing concentrations of 1-30 μg/ml of CFHR3 (0.02-0.6 μm) or CFHR1 (0.02-0.69 μm) or BSA, or CFHR1 plus CFHR3 (each 1 to 20 μg/ml, 0.02-0.46 μm). Binding of the proteins to C3b can be analyzed by flow cytometry.

EXAMPLES

Example 1 A Genome-Wide Association Study of IgA Nephropathy (IgAN)

A genome-wide association study of IgA nephropathy (IgAN) was conducted in 1,194 cases and 902 controls of Chinese Han ancestry, with targeted follow-up in Chinese and European cohorts comprising 1,950 cases and 1,920 controls. Three independent loci in the major histocompatibility complex (MHC), a common deletion of CFHR1 and CFHR3 at Chr. 1q32 and a locus at Chr. 22q12 that each surpassed genome-wide significance (p-values for association between $1.59 \times 10^{-26}$ and $4.84 \times 10^{-9}$ and minor allele odds ratios of 0.63-0.80) were identified. These five loci explain 4-7% of the disease variance and up to a 10-fold variation in interindividual risk. Many of the IgAN-protective alleles are known to impart increased risk of other autoimmune or infectious diseases, and IgAN protective allele frequencies closely parallel the variation in disease prevalence among Asian, European and African populations, suggesting complex selective pressures (all 10 protective alleles are identified in Table 2).

Study Design and Genotyping of Discovery Cohort.

To detect loci conferring susceptibility to IgAN, a two-stage GWAS was performed (Table 1). In the discovery phase, genome-wide genotyping was performed on the Illumina 610 quad platform in 1,228 biopsy-proven IgAN cases and 966 healthy controls of Chinese Han ancestry recruited from Beijing (Table 1). The top signals in the discovery phase were further evaluated in an independent cohort of Han Chinese descent (Shanghai cohort, 740 cases and 750 controls) and a European cohort of Italian and North American origin (combined by stratified analysis, 1,273 cases and 1,201 controls). Subsequently, the Beijing, Shanghai and European cohorts were analyzed together to identify genome-wide significant loci.

Genome-Wide Association Analysis.

Stringent quality control filters were applied in the analysis of genome-wide genotyping data that resulted in elimination of 5% of the samples due to low call rate, duplication, cryptic relatedness or gender mismatch and 16.8% of markers primarily due to low minor allelic frequency (<0.010. After quality control, the genotyping call rate was 0.9992. The standard 1-degree of freedom Cochran Armitage (CA) trend test was used to analyze 498,322 SNPs in the discovery cohort of 1,194 cases (650 males/544 females, average age 31.1 years) and 902 controls (608 males/294 females, average age 31.5 years). The quantile-quantile plot showed no global departure from the expected distribution of p-values and the inflation factor ($\lambda$) was 1.024, indicating negligible population stratification. Accordingly, principal component analysis (PCA) demonstrated that cases and controls were matched along the axes of significant principal components, and PCA correction did not substantially change the distribution of the association statistic or the genomic inflation factor ($\lambda$=1.022). Analysis indicated that the association results were not biased by differences in ancestry or population structure between cases and controls.

The genome-wide association analysis revealed 27 SNPs exceeding genome-wide thresholds for significance ($p \leq 5 \times 10^{-8}$). These 27 signals all resided in a 0.54 Mb interval within the major histocompatibility complex (MHC) on Chr. 6p21, with the top signal at rs9275596 ($p=1.9 \times 10^{-12}$). Interestingly, fourteen MHC SNPs with suggestive p-values ($5 \times 10^{-6}$ to $1 \times 10^{-4}$) showed little or no linkage disequilibrium with rs9275596 FIG. 1A.

Follow-Up of Top Signals from Discovery Stage

After removal of MHC SNPs, additional loci showing departure from the expected p-value distribution remained. Signals based on the false discovery rate were ranked and it was decided to follow-up loci with p-value$\leq 1.3 \times 10^{-5}$, corresponding to a q-value$\leq 0.10$.[20] Power calculations indicated that this strategy provides 80% power to detect loci with allelic frequencies>0.10 and relative risk>1.5 with genome-wide significance ($p<5\times10^{-8}$) in the combined cohort. In total, 65 SNPs from 10 distinct loci met these criteria (including three potentially independent loci in the MHC and two in the Chr. 22q12.2 interval). The top-scoring SNP's and one additional SNP from each of these intervals were genotyped in follow-up cohorts (total 20 SNPs in 3,870 individuals after quality control, table 1). Tests of association were performed within each cohort, followed by a combined analysis with the discovery cohort using Mantel's extension of CA trend test (Table 2).

Five of the ten loci selected for follow-up surpassed the threshold for significant genome-wide association: three loci within 6p21, one locus at 1q32, and one locus at 22q12.2 (Table 2,). Each signal demonstrated significant association with consistent effect size for the same protective allele in each individual cohort, with little evidence for heterogeneity.

Figure 1B:
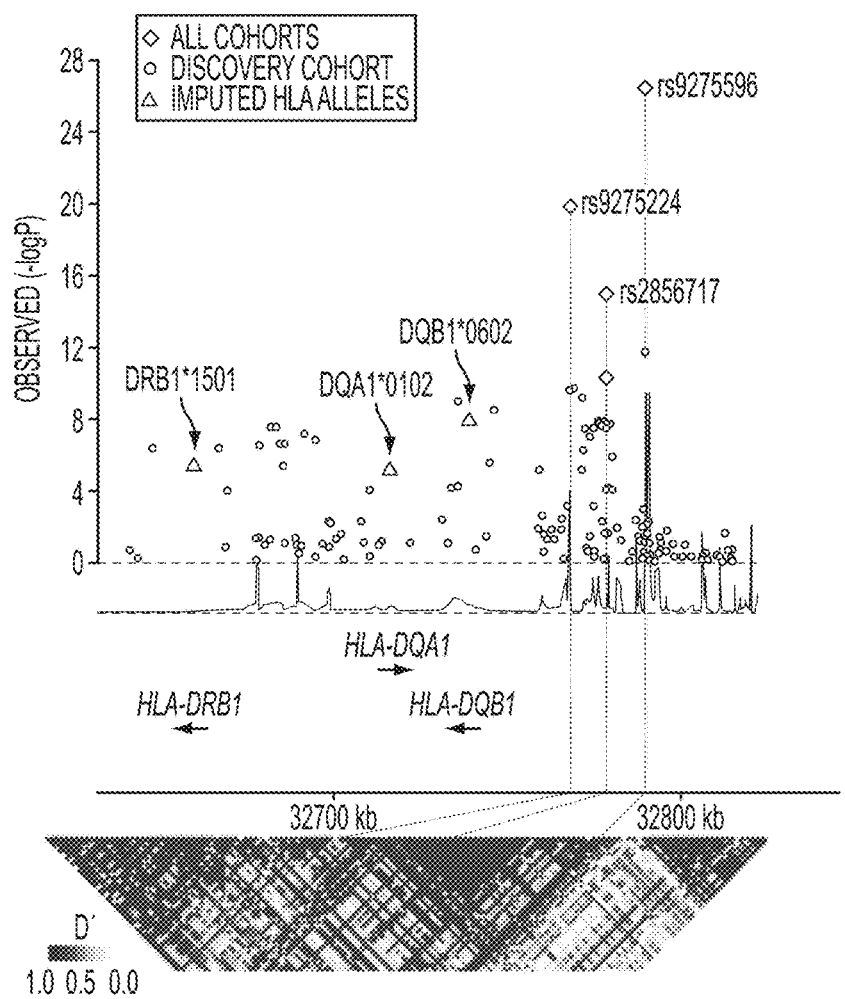

The strongest association in the combined cohort was a locus defined by rs9275596 within a ~170 kb interval that includes the HLA-DRB1, -DQA1, and -DQB1 genes (rs9275596), OR=0.63, $p=1.6\times10^{-26}$). SNP (rs9275596) achieves genome-wide significance with a consistent effect size in each cohort (Table 2, FIG. 1B) and has strong supporting association from a nearby SNP in strong LD (rs2856717). However, SNP (rs9275596) by itself did not explain all of the signal at 6p21.

Figure 1C:
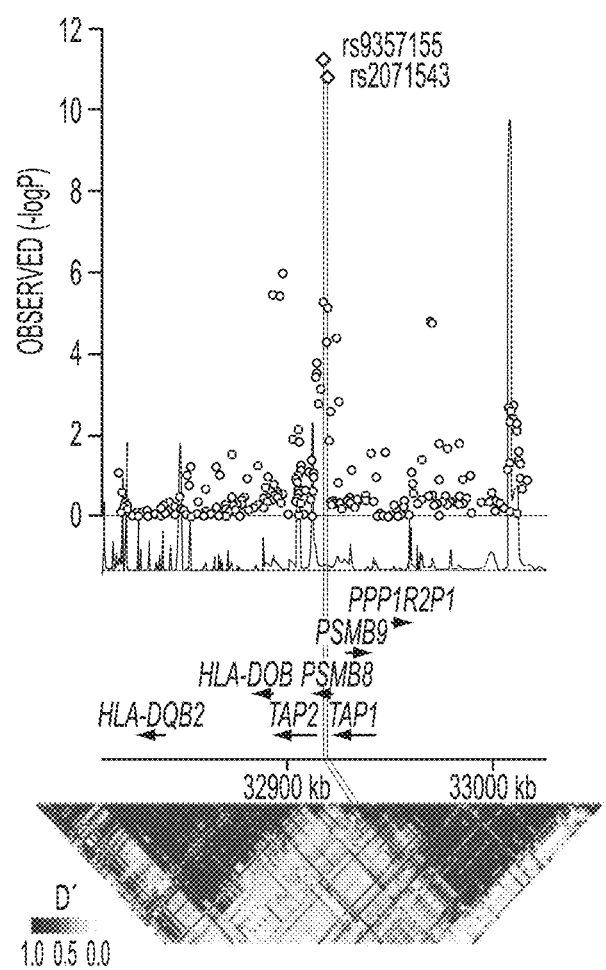

Conditioning for the effect of rs9275596 eliminated evidence of association for the majority of SNPs in close proximity to 6p21 however two distinct loci maintained genome-wide significance. The second independent locus is defined by rs9357155 (which has an $r^2=0.01$ with rs9275596 in the combined cohort) and shows an OR=0.74 and a p-value of $6.9\times10^{-9}$ for association with IgAN after conditional analysis (Table 3, FIG. 1C). SNP rs9357155 lies in a ~100 kb segment of LD and lies 128 kb centromeric to rs9275596. This LD segment contains the genes TAP2, TAP1, PSMB8, and PSMB9, and the supporting SNPs in this region (rs2071543) is a missense variant in PSMB8 (Q49K) that is at a position completely conserved among all orthologs (most distantly related ortholog is in platypus; Tables 2 and 3, FIG. 1C).

Figure 1D:
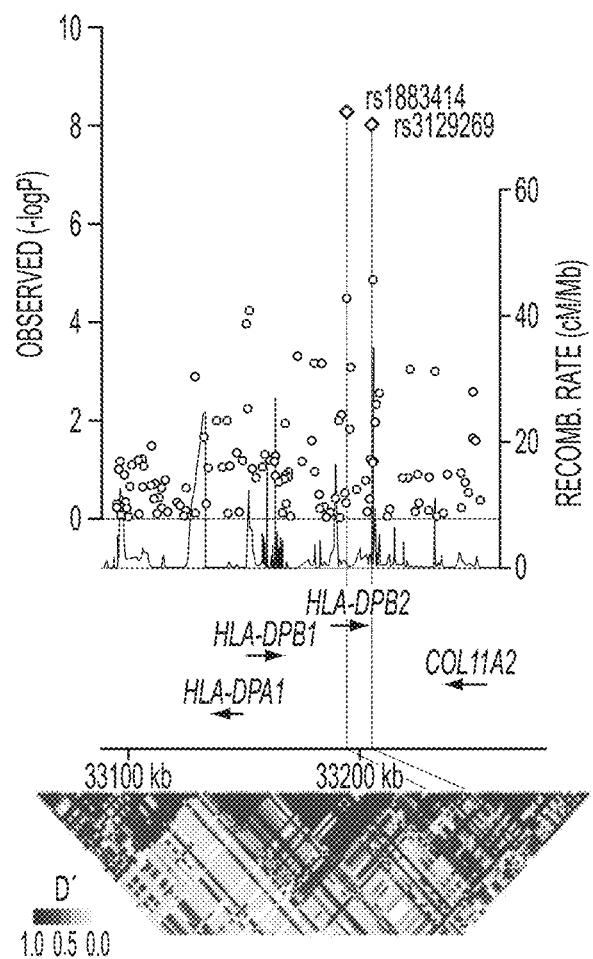

After conditioning for the effects of both rs9275596 and rs9357155, a third locus within the MHC defined by rs1883414, which lies 400 kb centromeric to rs9275596 and shows $r^2=0.005$ and 0.002 with rs9275596 and rs9357155, respectively, also shows a conditioned OR of 0.77 and p-value of $3.1\times10^{-8}$ for association (Table 3). This signal in the HLA-DPA1-DPB1-DPB2 region is supported by a second locus defined by SNP (rs3129269) and demonstrated consistent effect size across cohorts (Tables 2, 3, FIG. 1D).

To better delineate the risk associated with the MHC region and detect potential functional variants, classical HLA alleles were imputed in the discovery cohort.[21] This demonstrated a genome-wide significant association with a protein-altering variant of known functional significance, the DQB1*0602 allele (OR=0.47, $p=6.6\times10^{-9}$). DQB1*602 is in strong LD with another functional allele, DRB1*1501. However, conditional analysis showed that DQB1*602 best explained this association signal. The strength of the DQB1*602 association is probably underestimated due to the limitations of current imputation algorithms (sensitivity of 56.6% for detection of the DQB1*602 allele).

Figure 2B:
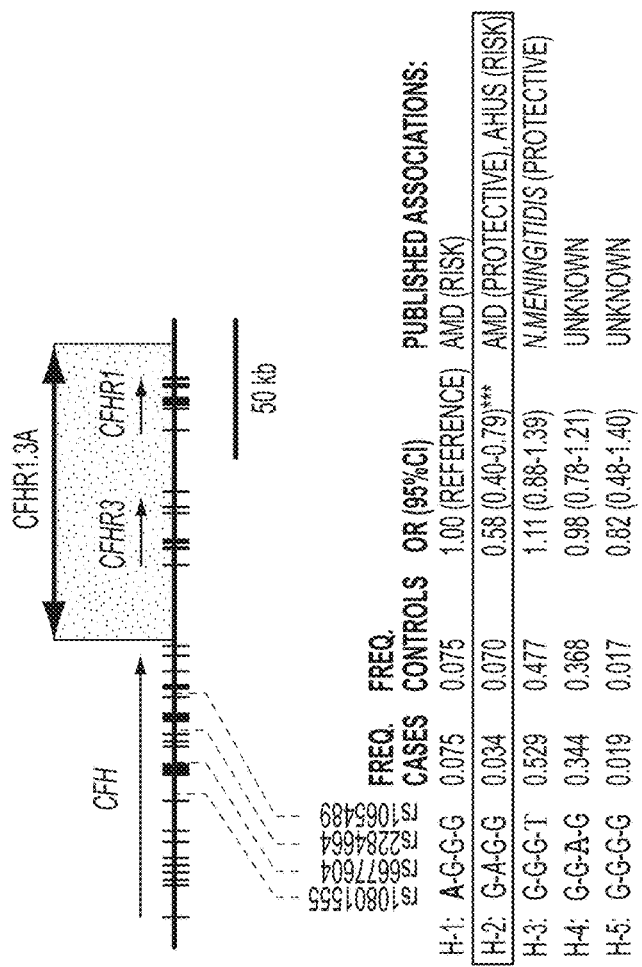
FIG. 2A-2C. Analysis of the Chr. 1 and Chr 22. loci.
Figure 2A:
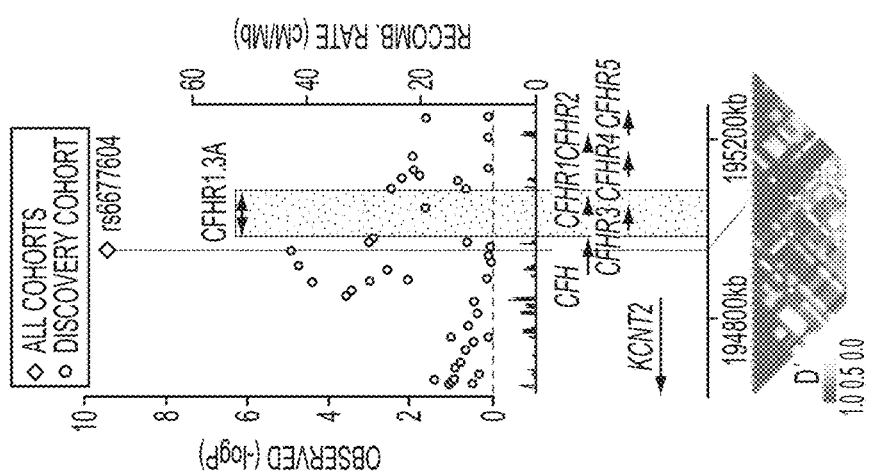

A major signal outside the MHC locus resided in a 100-kb segment on Chr. 1q31-q32.1 containing complement factor H (CFH) and the related CFHR3, CFHR1, CFHR4, CHFR2, CFHR5 genes (rs6677604, OR=0.68, $p=3.0\times10^{-10}$ in the combined cohort). This locus defined by rs6677604 was also the top signal in the genome-wide CNP analysis. SNP rs6677604, is located in intron 12 of CFH and is supported by multiple highly correlated SNPs (FIG. 2A, Table 2). After controlling for rs6677604, there were no other independent signals in the entire CFH region. The association results at rs6677604 were far less significant under a recessive model ($p=5.6\times10^{-5}$), which supports an additive risk. The rs6677604-A allele is protective in all three cohorts but has a much higher allele frequency in Europeans (0.23 in European controls vs. 0.07 in Chinese controls, Table 2). This allele perfectly tags a common deletion spanning the CFHR1 and CFHR3 genes (CFHR1,3Δ)[22,23]. The association of rs6677604-A allele with CFHR1,3Δ in the cohort tested was confirmed: PCR of multiple amplicons within CFHR1 and CFHR3 failed and the CFHR1 protein could not be detected in serum from all A/A homozygotes tested. Evidence for association of IgAN with alleles in CFH that confer risk of macular degeneration (AMD) was carefully evaluated and no contribution to risk was found (e.g., the Y402H variant, tagged by rs10801555, showed OR=1.0, $p=0.99$ in discovery cohort; FIG. 2B). Haplotype-based analysis in the Beijing discovery cohort demonstrated protection by the haplotype containing the rs6677604-A allele (OR=0.56, $p=1\times10^{-6}$ vs. all other haplotypes in the discovery cohort, FIG. 2B) but no significant effect of other haplotypes.

Figure 2C:
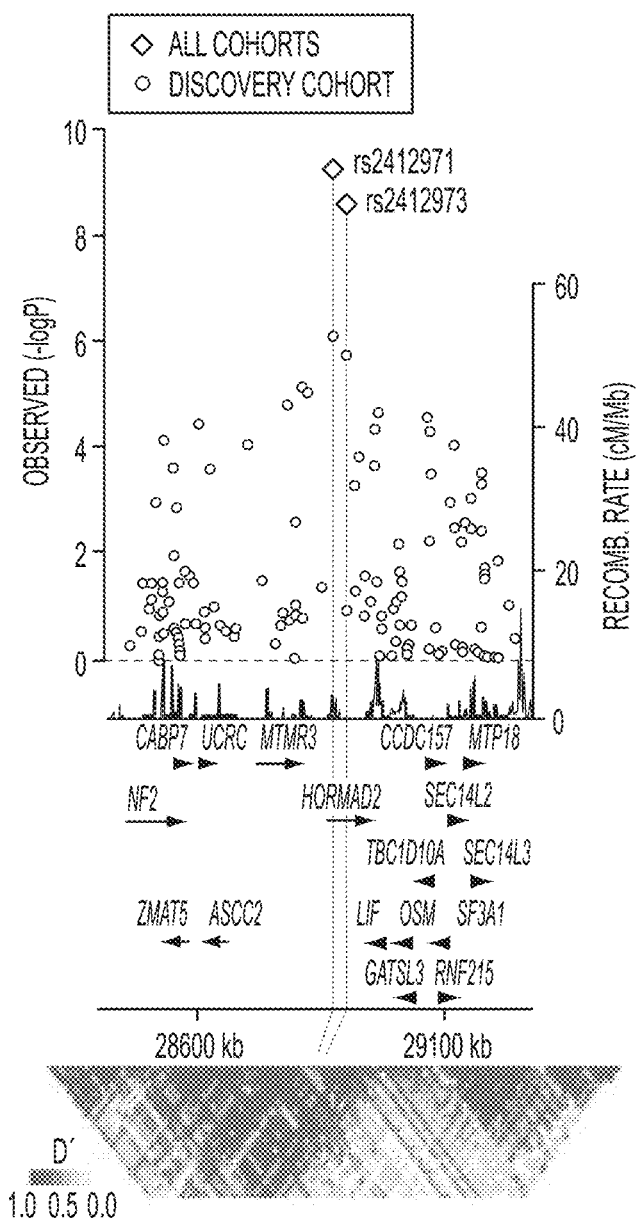

The fifth signal in the GWAS resided at a locus in an intronic SNP in HORMAD2 on Chr. 22.q12.2 defined by rs2412971 (OR=0.80, $p=1.9\times10^{-9}$) and was supported by a second SNP within 35 kb of this signal (rs2412973, OR=0.80, $p=4.5\times10^{-9}$). After controlling for rs2412971, there were no other independent signals in this region. The association extended across a large LD segment that encompasses genes including HORMAD2, MTMR3, LIF, and OSM (FIG. 2C).

Cumulative Effects on Disease Risk.

To determine the cumulative risk conferred by these loci, a genetic risk score was computed, calculated as the weighted sum of the number of independent protective alleles multiplied by the log of the odds ratio for each of the individual loci (Table 4). The disease risk varied up to 10-fold between individuals with no protective alleles compared those with five or more. The risk score model was similar in all cohorts and collectively explained 5-7% of the variation in disease risk in the Chinese cohorts and ~4% of the risk in the European cohort (Table 4). The risk score did not reproducibly correlate with any of the parameters of disease severity, such as estimated GFR, degree of proteinuria, or histologic severity grade.

Most interestingly, consistent with the known higher prevalence of IgAN in Asians, the frequency of protective alleles was significantly lower in the Chinese [Beijing and Shanghai cohorts] cohorts compared to the European group. The differences in the distribution of protective alleles were highly significant between the Asian and European cohorts ($p=4.8\times10^{-72}$ and $p=6.4\times10$ for differences within cases and controls, respectively). To confirm this finding in independent populations, three HapMap groups were examined and it was similarly found that frequencies of protective alleles correlated with disease frequency among these populations: protective allele frequencies were highest in Asians, intermediate in Europeans, and lowest in Africans. For example, the protective allele at the chromosome 1 locus showed a frequency of 0.08 in Asians, 0.24 in Europeans and 0.49 in Africans.

These five risk loci explained up to a ten-fold variation in interindividual risk and cumulatively accounted for 4-7% of the disease variance. The effect sizes at these loci are relatively large and consistent across the European and Chinese cohorts, with four having inverse OR≥1.4, which is comparable to those detected in previous studies of autoimmune or inflammatory diseases[21,24-30]. The protective allele frequencies also strongly paralleled the prevalence of IgAN among different populations.

There was a major signal in the MHC region, which was identified but not localized in a recent GWAS with 533 affected subjects[19]. The study herein revealed that this signal originated from three distinct loci within HLA and two additional non-HLA loci. Evidence supporting the presence of three independent risk loci on Chr. 6p21 includes their position within distinct LD segments, as well as genome-wide significance after conditioning for the other two loci, with consistent effects within each cohort.

The strongest HLA signal was in the HLA-DRB1/DQB1 region. Imputation of classical alleles suggested that this signal is fully or partially conveyed by a strong protective effect of the DRB1*1501-DQB1*0602 haplotype; the strength of this association was likely underestimated by limitations of imputation. This haplotype is relatively common in the European and Asian populations (frequency ~0.1-0.2) and in contrast to its protective effect for IgAN has been associated with increased risk of SLE[25], multiple sclerosis[31], narcolepsy[32] and hepatotoxicity from COX2 inhibitors[30] but is also highly protective for type I diabetes mellitus[26]. This haplotype is also protective in selective IgA deficiency[27], however there was no association with IgA levels at this locus among the examined cases. This region has a complex LD structure, and the conditional analysis used in these studies suggests the possibility of an independent signal within this region (at rs9275424).

The second independent interval at 6p21 contained TAP2, TAP1, PSMB8, and PSMB9, interferon-regulated genes that have been implicated in antigen generation and processing for presentation by MHC I molecules; they also play an important role in modulation of cytokine production and cytotoxic T-cell response[33,34]. PSMB8 expression is increased in PBMCs from IgAN subjects[35]. This locus has not been identified in any prior GWAS. The third signal at 6p21 comprised the HLA-DPA1, -DPB1, and -DPB2 genes. This locus is associated with risk of chronic hepatitis B infection[29] (a major clinical problem in China) and systemic sclerosis stratified for anti-DNA topoisomerase I or anticentromere autoantibodies[31], but the protective alleles associated with these phenotypes are not in LD with any of the IgAN protective alleles.

The results show unambiguous protective effect of the CFHR1,3Δ-containing haplotype in IgAN, strongly suggesting that CFHR1,3Δ is the functional variant. It is not clear how loss of CFHR1 and/or CFHR3 may confer protection for IgAN. Without being bound by theory, the protective effects may be due to the competing roles of CFH and CFHR1 proteins[37], such that loss of CFHR1 enhances CFH effects, reducing inflammation at tissue surfaces.

The Chr. 22q12.2 locus spans a large interval that contains OSM and LIF, encoding cytokines implicated in mucosal immunity and inflammation The rs2412973-A allele, which is protective for IgAN, has also been associated with increased risk of early-onset inflammatory bowel disease (IBD) and altered expression of MTMR3 expression in individuals with ulcerative colitis[28]. This finding is of interest given the known clinical association between IBD and secondary forms of IgAN. Lastly, the protective allele at this locus is also associated with lower serum IgA levels among cases ($p=3.9\times10$).

It is noteworthy that many of the protective alleles for IgAN have been implicated as risk factors other immune-mediated and infectious disorders, demonstrating that complex selection pressures (potentially balancing selection) influence the frequencies of these alleles among world populations.

Materials and Methods

Genome-wide genotyping, genotype quality control, and primary association analyses for these studies are described in REF Gharavi AG, Kiryluk K, Choi M, Li Y, Hou P, et al. (2011) Genome-wide association study identifies susceptibility loci for IgA nephropathy. Nat Genet. After quality control analysis, the discovery cohort consisted of 1,194 cases and 902 controls genotyped with the Illumina Human 610-Quad BeadChip. The primary genome-wide association analyses were performed using PLINK v1.07[44]. A standard 1-df Cochran-Armitage trend test was the primary association test, as it demonstrates greater robustness to deviations from Hardy-Weinberg equilibrium compared to its alternatives. The per-allele odds ratios were estimated and 95% confidence intervals for all tested SNPs. The genome-wide distributions of p-values were examined using qq-plots, before and after exclusion of the HLA region.

FDR and Power Analysis:

The calculation of positive false discovery rate (pFDR) was performed using the q-value package (R). The proportion of SNPs that were truly null ($\Pi_o$) was estimated at 0.991 using the empiric distribution of genome-wide p-values[20]. The q-value of 0.10 (positive FDR of 10%) corresponded to the p-value of $1.3\times10^{-5}$. This q-value threshold defined 65 top SNPs that were subsequently analyzed for replication. The power analysis was performed using methods developed by Skol et al[45]. The calculations were performed under the following assumptions: disease prevalence 1%, additive risk model, stage I (discovery) sample size of 1000 cases and 1000 controls, stage II (follow-up) sample size of 2000 cases and 2000 controls, follow-up significance threshold of $1.3\times10^{-5}$, and joint (stage I and II) significance level of $5\times10^{-8}$. The joint power of our study design was calculated for a range of disease allele frequencies (0.10-0.50) and effect sizes (GRR 1.10-1.80). The effect sizes that are detectable at alpha $5\times10^{-8}$ and power 0.80 in the joint analysis were estimated using CaTS software[45].

Selection of SNPs for Follow-Up:

The 65 SNPs that reached our q-value threshold were first clustered into 10 distinct loci based on their physical location and regional patterns of LD. The correctness of genotype calls was verified for each SNP individually, by visual inspection of the Illumina cluster plots. Conditional logistic regression analysis was performed to confirm correct SNP grouping and detect independence signals. These analyses suggested 3 distinct loci on chromosome 6p21 and 2 distinct loci on chromosome. 22q12.2. The SNP's with the lowest p-value within each locus was selected for follow-up. The selection of the second SNP for back-up genotyping was based mainly on its strength of association, high LD with the top-scoring SNP in European and Chinese HapMap populations, robustness of Illumina clustering plots, and high genotyping rate. In total, we selected 20 representative SNPs for genotyping in 2,013 cases and 1,951 controls recruited for stage 2 of the study.

Association Analyses Across Multiple Cohorts:

Result across multiple cohorts were combined using a stratified trend test with Mentel's extension of the Cochran-Armitage test (SNPMatrix package, R)[46]. Heterogeneity across cohorts was tested with the heterogeneity index ($I^2$), and by performing Cochrane's Q heterogeneity test. In order to ensure findings were robust to methodology, we also combined the per-allele effect estimates using Cochran-Mantel-Haenszel stratified analysis, as well as an inverse variance-weighted method under a fixed-effects model. The results were concordant regardless of the meta-analytic method used.

Conditional Analyses:

A stepwise logistic regression was performed after controlling for the genotypes of the conditioning SNPs using PLINK (v1.07). The adjusted (conditioned) effect estimates were then combined across cohorts by adding cohort information as an additional covariate in the stratified analysis (Table 3). Similar approach was used for the conditional analysis of classical HLA alleles.

Haplotype-Based Association at CFH Locus:

These analyses were performed in PLINK v.1.07. Haplotypes were phased across the CFH locus in the Beijing cohort (FIG. 2B) and haplotype frequencies were estimated in the cases and controls separately, as well as jointly in the entire cohort. Only the haplotypes with the overall frequency greater than 1% were included in association analyses. The p-values were derived for tests of association of one haplotype versus all others. The odds ratios and the corresponding 95% confidence intervals were estimated in reference to the AMD risk haplotype (H-1, FIG. 2B) which has an identical frequency between cases and controls.

Imputation and Association Analysis of Classical HLA Alleles:

The HLA classical alleles at DQB1, DQA1 and DRB1 loci were imputed based on the genotype data from the Beijing cohort. In short, the genotype data were first phased using BEAGLE[47] and pairwise IBD status was determined using the GERMLINE software[48]. The HLA classical allele status and genotype data of the HapMap Han Chinese individuals were utilized as a reference panel[21] using the HLA-via-IBD software. The accuracy of the imputation procedure was tested by direct sequencing of the informative coding segments of HLA-DQB1 gene in a random subset of 420 samples. This demonstrated that imputation had 57% sensitivity and 96% specificity for identifying the HLA-DQB1*602 alleles.

Risk Score Discovery and Validation:

Among the 5 independent regions of association, alleles with lower frequency conveyed a protective effect. Therefore, the risk score model was based on protective alleles for the top five independent and most strongly associated SNPs (rs9275596, rs9357155, rs1883414, rs2412971, and rs6677604). A Risk Score can also be determined based on the five redundant alleles. The Risk Score was calculated as a weighted sum of the number of protective alleles at each locus multiplied by the log of the odds ratio for each of the individual loci for a specific cohort. Only individuals with non-missing genotypes for all 10 alleles were included in this analysis (Table 4). The same method is used for calculating a risk score that includes the two protective alleles discovered in the second study described in Example 2.

The predictive risk score models were built using association results for each of the three model-building cohorts and were validated by testing their predictive properties against all other cohorts (target cohorts). The percent of the total variance in disease state explained by the risk score was estimated by Nagelkerke's pseudo R-squared from the logistic regression model with the risk score as a quantitative predictor and disease state as an outcome. The C-statistic was estimated as an area under the ROC curve provided by the above logistic model. These analyses were performed with SPSS Statistics version 17.0.

Distributions of Protective Alleles:

Each individual study participant was scored for the number of protective alleles and the distributions of protective alleles were compared between various ethnic groups. Only individuals with complete genotype information were included. Because relatively few individuals had 5 or more protective alleles, they were binned into a single category for the purpose of statistical testing and a chi-square goodness-of-fit test was used to derive p-values. Analysis of the HapMap release 23 dataset included 30 unrelated individuals from Yoruba in Ibadan, Nigeria (YRI), 30 unrelated Utah residents with ancestry from northern and western Europe (CEU), and a combined group of 45 unrelated Japanese individuals from Tokyo, Japan (JPT) and 45 Han Chinese from Beijing, China (CHB). The genotype data were downloaded directly from the HapMap Project website.

Common Copy Number Polymorphisms (CNP) Analysis:

For the purpose of this analysis, publicly available CNP discovery data were used that were obtained with 2.1-million NimbleGen CGH arrays by Conrad et al[49,50]. 1,051 SNPs present on the Illumina HumanHap 610K chip that tag known common (>1%) CNVs at $r^2>0.8$. The genotypes for these SNPs were extracted from the dataset and analyzed separately for association with the disease state. These SNPs underwent all QC steps as outlined above prior to association analysis. A simple 1-df chi-sq allelic test was used to screen for association (PLINK) and the results were ranked and visualized using a quantile-quantile plot (R). The top associated CNPs were validated using quantitative real-time PCR.

Quantitative Real-Time PCR:

qPCR was performed on genomic DNA using the iQ5 Real-Time PCR Detection System (Bio-Rad) and amplification was achieved using SYBR Green Supermix (Bio-Rad) with a standard 2-step amplification protocol. All samples were analyzed in triplicates. Three amplicons spanning CFHR1 and CFHR3 were tested and the signal was normalized to an amplicon in B-actin. Pooled DNA from 10 individuals homozygous for G alleles at rs6677604 was used as reference.

Western Blotting:

Diluted plasma samples were separated on 4-15% Ready Gel (Bio-Rad, Hercules, Calif.), transferred to PVDF Membranes (Millipore, Billerica, Mass.), and protein blotted with primary antibodies against CFH (AbD Serotec, Raleigh, N.C.) and CFHR1 (R&D Systems, Minneapolis, Minn.) using standard protocols.

Genome-Wide Genotyping, Genotype Quality Control, and Primary Association Analyses:

After quality control analysis, the discovery cohort consisted of 1,194 cases and 902 controls genotyped with the Illumina Human 610-Quad BeadChip. The primary genome-wide association analyses were performed using PLINK v1.07[1]. A standard 1-df Cochran-Armitage trend test was used as the primary association test, as it demonstrates greater robustness to deviations from Hardy-Weinberg equilibrium compared to its alternatives. The per-allele odds ratios and 95% confidence intervals were estimated for all tested SNPs. The genome-wide distributions of p-values were examined using qq-plots, before and after exclusion of the HLA region.

FDR and Power Analysis:

The calculation of positive false discovery rate (pFDR) was performed using the q-value package (R). The proportion of SNPs that were truly null (Ho) was estimated at 0.991 using the empiric distribution of genome-wide p-values[2]. The q-value of 0.10 (positive FDR of 10%) corresponded to the p-value of $1.3 \times 10^{-5}$. This q-value threshold defined 65 top SNPs that were subsequently analyzed for replication. The power analysis was performed using methods developed by Skol et al[3]. The calculations were performed under the following assumptions: disease prevalence 1%, additive risk model, stage I (discovery) sample size of 1000 cases and 1000 controls, stage II (follow-up) sample size of 2000 cases and 2000 controls, follow-up significance threshold of $1.3 \times 10^{-5}$, and joint (stage I and II) significance level of $5 \times 10^{-8}$. The joint power of our study design. was calculated for a range of disease allele frequencies (0.10-0.50) and effect sizes (GRR 1.10-1.80). The effect sizes that are detectable at alpha $5 \times 10^{-8}$ and power 0.80 in the joint analysis were estimated using CaTS software[3].

Selection of SNPs for Follow-Up:

The 65 SNPs that reached our q-value threshold were first clustered into 10 distinct loci based on their physical location and regional patterns of LD. The correctness of genotype calls was verified for each SNP individually, by visual inspection of the Illumina cluster plots. Conditional logistic regression analysis was performed to confirm correct SNP grouping and detect independence signals. These analyses suggested 3 distinct loci on chromosome. 6p21 and 2 distinct loci on chromosome. 22q12.2. The SNP's with the lowest p-value within each locus was selected for follow-up. The selection of the second SNP for back-up genotyping was based mainly on its strength of association, high LD with the top-scoring SNP in European and Chinese HapMap populations, robustness of Illumina clustering plots, and high genotyping rate. In total, 20 representative SNPs were selected for genotyping in 2,013 cases and 1,951 controls recruited for stage 2 of the study.

Association Analyses Across Multiple Cohorts:

Result across multiple cohorts were combined using a stratified trend test with Mentel's extension of the Cochran-Armitage test (SNPMatrix package, R)[4]. Heterogeneity was tested across cohorts with the heterogeneity index ($I^2$), and by performing Cochrane's Q heterogeneity test. In order to ensure findings were robust to methodology, the per-allele effect estimates were also combined using Cochran-Mantel-Haenszel stratified analysis, as well as an inverse variance-weighted method under a fixed-effects model. The results were concordant regardless of the meta-analytic method used.

Conditional Analyses:

Stepwise logistic regression was performed after controlling for the genotypes of the conditioning SNPs using PLINK (v1.07). The adjusted (conditioned) effect estimates were then combined across cohorts by adding cohort information as an additional covariate in the stratified analysis (Table 3). Similar approach was used for the conditional analysis of classical HLA alleles.

Haplotype-Based Association at CFH Locus:

The genotype data of the Beijing cohort was extracted and the haplotypes were phased across the CFH locus (FIG. 2B). The haplotype frequencies were estimated in the cases and controls separately, as well as jointly in the entire cohort. Only the haplotypes with the overall frequency greater than 1% were included in association analyses. The p-values were derived for tests of association of one haplotype versus all others. The odds ratios and the corresponding 95% confidence intervals were estimated in reference to the AMD risk haplotype (H-1, FIG. 2B) which has an identical frequency between cases and controls. These analyses were performed in PLINK v.1.07.

Imputation and Association Analysis of Classical HLA Alleles:

The HLA classical alleles at DQB1, DQA1 and DRB1 loci were imputed based on the genotype data from the Beijing cohort. In short, the genotype data was first phased using BEAGLE[5] and pairwise IBD status was determined using the GERMLINE software[6]. The HLA classical allele status and genotype data of the HapMap Han Chinese individuals was utilized as a reference panel. The imputation was performed using the HLA-via-IBD software. The accuracy of the imputation procedure was tested by direct sequencing of the informative coding segments of HLA-DQB1 gene in a random subset of 420 samples. This demonstrated that imputation had 57% sensitivity and 96% specificity for identifying the HLA-DQB1*602 alleles. Risk score discovery and validation:

Among the 5 independent regions of association, alleles with lower frequency conveyed a protective effect. Therefore, the risk score model was based on protective alleles for the top five independent and most strongly associated SNPs (rs9275596, rs9357155, rs1883414, rs2412971, and rs6677604). The Risk Score was calculated as a weighted sum of the number of protective alleles at each locus multiplied by the log of the odds ratio for each of the individual loci for a specific cohort. Only individuals with non-missing genotypes for all 10 alleles were included in this analysis (Table 4). The predictive risk score models were built using association results for each of the three model-building cohorts and were validated by testing their predictive properties against all other cohorts (target cohorts). The percent of the total variance in disease state explained by the risk score was estimated by Nagelkerke's pseudo R-squared from the logistic regression model with the risk score as a quantitative predictor and disease state as an outcome. The C-statistic was estimated as an area under the ROC curve provided by the above logistic model. These analyses were performed with SPSS Statistics version 17.0.

Distributions of Protective Alleles:

Each individual study participant was scored for the number of protective alleles and the distributions of protective alleles were compared between various ethnic groups. Only individuals with complete genotype information were included. Because relatively small number of individuals had 5 or more protective alleles, they were binned into a single category for the purpose of statistical testing and a chi-sq goodness-of-fit test was used to derive p-values. Analysis of the HapMap release 23 dataset included 30 unrelated individuals from Yoruba in Ibadan, Nigeria (YRI), 30 unrelated Utah residents with ancestry from northern and western Europe (CEU), and a combined group of 45 unrelated Japanese individuals from Tokyo, Japan (JPT) and 45 Han Chinese from Beijing, China (CHB). The genotype data was downloaded directly from the HapMap Project website.

Common Copy Number Polymorphisms (CNP) Analysis:

For the purpose of this analysis, we utilized publicly available CNP discovery data obtained with 2.1-million NimbleGen CGH arrays by Conrad et al[8, 9]. 1,051 SNPs were present on the Illumina HumanHap 610K chip that tag known common (>1%) CNVs at $r^2 > 0.8$. The genotypes for these SNPs were extracted from the dataset and analyzed separately for association with the disease state. These SNPs underwent all QC steps as outlined above prior to association analysis. A simple 1-df chi-sq allelic test was used to screen for association (PLINK) and the results were ranked and visualized using a quantile-quantile plot (R). The top associated CNPs were validated using quantitative real-time PCR.

Quantitative Real-Time PCR:

qPCR was performed on genomic DNA using the iQ5 Real-Time PCR Detection System (Bio-Rad) and amplification was achieved using SYBR Green Supermix (Bio-Rad) with a standard 2-step amplification protocol. All samples were analyzed in triplicates. Three amplicons spanning the CFHR1 and CFHR3 were tested and the signal was normalized to an amplicon in B-actin. Pooled DNA from 10 individuals homozygous for G alleles at rs6677604 was used as reference.

Western Blotting:

Diluted plasma samples were separated on 4-15% Ready Gel (Bio-rad), transferred to PVDF Membranes (Millipore), and protein blotted with primary antibodies against CFH (AbD Serotec) and CFHR1 (R&D Systems) using standard protocols.

Example 2 Eight Cohort Replication Study

Replication Study Methods:

For replications eight cohorts (five European, two East Asian, and one African-American cohort, totaling 2,228 cases and 2,561 controls were examined. While each individual cohort at best had 40-50% power to replicate original GWAS findings, the combined replication cohort (2,228 cases and 2,561 controls) provided essentially 100% power for replication across the range of alleles frequencies and odds ratios initially observed.

The two top-scoring SNPs were genotyped for the CFHR3/R1, TAP2/PSMB9, DPA1/DPB2, and HORMAD2 loci, but four SNPs were included for the DQB1/DRB1 locus to test for independent alleles at this interval by conditional analysis. After a standard assessment of genotype quality control, association testing was performed within each cohort using the standard Cochrane-Armitage trend test. Testing was also done for heterogeneity of associations and performed a meta-analysis under both fixed and random effects models (Table 5).

Four of the five original GWAS loci displayed significant replication with direction-consistent ORs and no heterogeneity comparable to the original findings (Table 5). The strongest replication was at the DQB1/DRB1 locus and achieved genome-wide significance in the replication cohort (fixed effects OR 0.75, P-value $4 \times 10^{-11}$). The CFHFR3/R1 locus on Chr.1q32, the HORMAD2 locus on Chr.22q12, and the DPA1/DPB2 locus on Chr.6p21 were also robustly replicated (fixed effects p-values $3 \times 10^{-3} - 7 \times 10^{-7}$), with minimal between-cohort heterogeneity ($I^2 < 25\%$). Accordingly, when combined with the four cohorts studied in the original GWAS, these four loci provided highly significant evidence of association (fixed effects p-values $3 \times 10^{-10} - 5 \times 10^{-32}$).

In contrast, the TAP2/PSMB9 locus on Chr. 6p21 displayed direction-consistent replication only in the Italian, German, Czech, and Japanese cohort but the full replication cohort did not support this association (Tables 1 and 9). However, when combined with the four cohorts from the original GWAS, this locus remained genome-wide significant (fixed effects p-values $1 \times 10^{-8}$ and $6 \times 10^{-10}$ for rs9357155 and rs2071543, respectively Table 5). As expected, $I^2$ and Q-tests provided evidence of heterogeneity and random effects meta-analysis, which explicitly models heterogeneity, was 1-3 orders of magnitude more significant than fixed effect meta-analysis at this interval (e.g. random effects p-value $3 \times 10^{-11}$, $I^2 = 61\%$ for rs9357155 Table 5). The heterogeneity was not attributable to differences in ethnicity or cohort size as the association results varied within Asian and European cohorts of differing size. Table 9.

Conditional Analysis Reveals New Independent Protective Alleles within the HLA-DQB1/DRB1 Locus:

The top signals in the original GWAS (Example 1), represented by rs9275596 and located within the DQB1/DRB1 locus, were mediated by a very strong protective effect of the DRB1*1501-DQB1*602 haplotype. The SNPs in this interval are in incomplete LD, and conditional analyses in this study and in an independent study of Europeans [10] had indicated that additional independent haplotypes also contributed to the signal. Additional SNPs that were in partial LD with rs9275596 were examined to detect potentially independent effects (rs9275224, rs2856717 and rs9275424, which had an $r^2$ of 0.09 to 0.7 with rs9275596. Table 10. After mutually conditioning each SNP on the remaining SNPs, three of the four SNPs in the DQB1/DRB1 region exhibited a genome-wide significant independent effect (rs9275596, rs9275224 and rs2856717, conditioned p-vales<$5 \times 10^{-8}$. Table 6 presents replication study results and combined meta-analysis. Combined association results for 12 SNPs representing 5 independent regions that reached genome-wide significance in the original GWAS. The combined effect estimates (per allele odds ratios) in the replication cohorts were all direction-consistent with the ones in the original GWAS cohorts. Significant heterogeneity was noted only for the second HLA locus represented by rs9357155 and rs2071543. Results show that the conditioned effect of the minor allele of rs2856717 was reversed compared to the crude effect estimate, suggesting that the adjustment for LD structure has uncovered a risk haplotype in this region (conditioned OR 1.61,p=$2 \times 10^{-10}$).

The above data indicated that there are multiple risk haplotypes within the DQB1/DRB1 locus. To better define these findings, four-SNP haplotypes at this locus were phased and associations with disease were tested (Table 7). There was a very strong protective effect of the ATAC haplotype (freq. 0.21) which, based on our previous imputation analysis, carries the DRB1*1501/DQB1*602 classical alleles. In addition, a new protective haplotype (ACAT, freq. 0.13) and a new risk haplotype (ATAT, freq. 0.05) were defined. The ATAC protective haplotype and the ATAT risk haplotype differ only by the rs9275596-C/T allele, explaining the reversal of OR for the rs2856717-T allele after conditioning for rs9275596 (Table 7). Additionally, the GCGT risk haplotype, tagged by the rs9275424-G allele, exhibited a weaker protective effect. These results were supported by both Asian and European cohorts. There are at least three independent haplotypes conferring risk of IgAN within this region. Further support is provided by the global haplotype association test, which achieved a p-value of $3 \times 10^3$ and thus was at least eleven orders of magnitude more significant than the individual SNP association tests at this locus.

These three independent haplotypes in-DQB1/DRB1 locus still did not explain associations in other Chr. 6p21 regions (TAP2/PSMB9 and DPAHDPB2 loci, respectively represented by rs9357155 and rs1883414), and a fully adjusted model that included all independently associated SNPs continued to support the original GWAS findings of three discrete genome-wide significant intervals on Chr. 6p21 (Table 11). First-order Interaction Screen Reveals Significant Interaction between CFHR3/R1 and HORMAD2 Loci:

All possible pairwise interactions between the seven risk-contributing SNPs were studied (Table 12). There was strong evidence for a multiplicative interaction (defined as departure from additivity on the log-odds scale) between the CFHR3/R1 (rs6677604) and the HORMAD2 loci (rs2412971). In this interaction, the rs2412971-A allele has a strong and consistent protective effect among all genotypic subgroups, but its effects are reversed among homozygotes for the rs6677604-A allele, which closely tags a CFHR3/R1 deletion (FIG. 3, Table 12). The significance of this interaction (p=2.5×10$^{-4}$) exceeds a Bonferroni-corrected threshold, and is most discernible among the European cohorts (p=1.4×10$^{-3}$), where both SNPs have higher minor allele frequencies. The 4-df genotypic interaction test was also significant for these two loci (p=6.4×10), but the 1-df multiplicative interaction model provided a better fit.

Seven Allele Test: Refined Genetic Risk Score

The risk score based on the five loci in the GWAS study was revised by incorporating the newly discovered independent effects of rs9275224 and rs2856717 and the interaction between the CFHR3/R1 and the HORMAD2 loci. The seven loci/protective alleles are: either rs6677604 or rs3766404], rs9275596, rs9275224, rs2856717, [either rs9357155 or rs2071543], [either rs1883414 or rs3129269] and [either rs2412971 or rs2412973]. A stepwise regression algorithm in the entire cohort defined a new risk score that retained the seven SNPs exhibiting an independent effect as well as the rs6677604*rs2412971 interaction term. A genetic risk score based on seven SNPs was more strongly associated with disease risk and explained a greater proportion of the disease variance in both the replication and the original GWAS (Example 1) dataset (Table 8). Moreover, the refined risk score was a highly significant predictor of disease in each individual replication cohort (Table 13). In all datasets combined, the new risk score explained 4.7% in disease variance and was 13 orders of magnitude more significant than score base on 5 SNPs identified in Example 1. In this model, one standard deviation increase in the score was associated with nearly 50% increase in the odds of disease (OR=1.47, 95% CI: 1.42-1.54, P=1.2×10$^{-72}$). This translates into nearly a 5-fold increase in risk between individuals from the opposing extremes of the risk score distribution (with tails defined by ≥2 standard deviations from the mean).

Study Cohorts:

The case-control cohorts analyzed in this study were contributed by clinical nephrology centers across Europe, Asia, and North America. All cases carried a biopsy diagnosis of IgAN defined by typical light microscopy features and predominant IgA staining on kidney tissue immunofluorescence, in the absence of liver disease or other autoimmune conditions. Each individual cohort of cases was accompanied by a control cohort of similar size, matched based on self-reported ethnicity and recruited from the same clinical center.

Genotyping and Genotype Quality Control:

The genotyping was performed by KBiosciences (Hoddeston, England). and genotype calls were determined using an automated clustering algorithm the (SNP Viewer v.1.99, KBiosciences, 2008). The genotype clusters were also examined visually across all plates, to assure lack of technical artifacts. The overall genotyping rate across all samples was 98.2%. For quality control we calculated minor allele frequencies, as well as per-SNP and per-individual rates of missingness within each case-control cohort separately. Additionally, we tested for Hardy-Weinberg equilibrium among the control groups from each cohort to assure lack of bias due to genotyping artifacts or population stratification. All SNPs included in the final analyses had minor allele frequency greater than 1%, per-SNP missingness rate less than 5%, and all passed the HWE test in controls (p>1×10$^{-2}$). Individuals with more than 2 missing genotypes out of the 12 loci were also excluded from the analysis.

Haplotype-Based Association Tests:

These analyses were carried out in PUNK v1.07 [35]. Haplotypes were first phased using EM algorithm across the HLA-DQB1, HLA-DQA1, HLA-DRB1 region. The haplotype frequencies were estimated in the cases and controls separately, as well as jointly in the entire cohort. Only common haplotypes with overall frequency >1% were included in the association tests. Global haplotype association test was performed using a $\chi^2$ test with n−1 degrees of freedom for n common haplotype groups. The ORs and the corresponding 95% confidence intervals were estimated in reference to the most common haplotype (GCAT, frequency ~35%).

First-Order Interaction Analyses:

To explore the possibility of interactions between the 7 independent risk variants, we screened all possible pairwise interaction terms for association with disease within the framework of logistic regression models (R version 2.10). As a screening test, we used 1-df LRT to compare two nested models: one with main effects only and one with main effects and a multiplicative (logit-additive) interaction term. We included cohort membership as a fixed covariate in both of these models. For this analysis we selected a Bonferroni-adjusted significance of 2.4×10$^{-3}$, a conservative threshold that accounts for all 21 pairwise interaction terms tested. Significant interactions from this analysis were also tested using a 4-df genotypic interaction test. In this test, we compared a model with allelic effects, dominant effects, and their interaction terms with a reduced model with no interaction terms. We followed the coding proposed by Cordell and Clayton: for each SNP i we modeled its allelic effect $x_{ia}$ by coding the genotypes AA, AB, and BB as $x_{ia}$=−1, 0, 1; we modeled dominance effects as $x_{id}$=−0.5, 0.5, −0.5 for the genotypes AA, AB, and BB, respectively [38].

Distributions of Protective Alleles and Risk Score Analyses:

Each study participant was scored for the number of risk alleles and the distributions of protective alleles were compared between cohorts of different ethnicity. Only individuals with complete genotype information at the 7 scored loci (14 alleles) were included in this analysis. The distributions were analyzed separately for cases and controls. A $\chi^2$ goodness-of-fit test was used to derive p-values for comparison of distributions. Because of a relatively small number of individuals at the tails of the distributions, for the purpose of statistical testing the tails of the distributions were binned into single-bin categories to achieve expected cell counts >5.

To confirm the results of conditional analyses and refine the genetic risk score proposed in the original GWAS, we subjected the genotype data from the entire cohort to a stepwise regression algorithm that selects significant covariates for the best predictive regression model based on Bayesian Information Criterion (the step function, R version 2.10). At model entry, we included all 12 genotyped SNPs, all 21 tested interactions, as well as cohort membership as a fixed covariate. Consistent with the results of our conditional analysis, the stepwise algorithm retained only the 7 SNPs exhibiting an independent effect along with the rs6677604*rs2412971 interaction term. All other terms were automatically dropped from the regression model.

The risk score was calculated as a weighted sum of the number of protective alleles at each locus multiplied by the log of the OR for each of the individual loci from the final fully adjusted model. Only individuals with non-missing genotypes for all 14 alleles were included in this analysis. The risk score was standardized across all populations using a z-score transformation, thus the standardized score represented the distance between the raw score and the population mean in units of standard deviation. The percentage of the total variance in disease state explained by the risk score was estimated by Nagelkerke's pseudo $R^2$ from the logistic regression model with the risk score as a quantitative predictor and disease state as an outcome. The C-statistic was estimated as an area under the receiver operating characteristic curve provided by the above logistic model. These analyses were carried out with SPSS Statistics version 19.0.

There were pronounced differences in the distributions of protective alleles among the three different ethnicities studied, with Asian controls carrying the highest number of protective alleles and African-Americans controls, the lowest. Global geographic variation in the genetic risk for IgAN was studied by applying the newly refined IgAN risk score in 6,319 healthy individuals across 85 worldwide populations. Marked differences were seen in the genetic risk across the world. Overall, the mean standardized risk score was lowest for Africans, intermediate for Middle Easterners and Europeans, and highest for East Asians and Native Americans.

TABLE 1

Summary of Study Cohorts

| | | Genotyped | | After QC | |
|---|---|---|---|---|---|
| Cohort | Ethnicity | Cases | Controls | Cases | Controls |
| Discovery Cohort | Han Chinese | 1,228 | 966 | 1,194 | 902 |
| Follow-up Cohort 1 | Han Chinese | 740 | 750 | 712 | 748 |
| Follow-up Cohort 2 | European | 1,273 | 1,201 | 1,238 | 1,172 |
| All Cohorts Combined: | | 3,241 | 2,917 | 3,144 | 2,822 |

TABLE 2

Association results for 10 SNPs representing 5 independent regions that reach genome-wide significance in combined analyses.

| Chr | Location (kb) | SNP (minor allele) | Beijing Discovery Cohort[a] N = 2,096 (1,194 cases/902 controls) | | | Shanghai Replication Cohort[a] N = 1,460 (712 cases/748 controls) | | | European Replication Cohort[b] N = 2,410 (1,238 cases/1,172 controls) |
|---|---|---|---|---|---|---|---|---|---|
| | | | MAF (cases/controls) | OR | P-value | MAF (cases/controls) | OR | P-value | MAF (cases/controls) |
| 1 | 194,918 | rs3766404 (C) | 0.052/0.086 | 0.59 | $1.84 \times 10^{-5}$ | 0.078/0.080 | 0.98 | $8.18 \times 10^{-1}$ | 0.12/0.14 |
| 1 | 194,953 | rs6677604 (A) | 0.041/0.073 | 0.55 | $1.20 \times 10^{-5}$ | 0.052/0.070 | 0.73 | $3.22 \times 10^{-2}$ | 0.17/0.23 |
| 6 | 32,778 | rs2856717 (T) | 0.19/0.26 | 0.66 | $3.31 \times 10^{-8}$ | 0.14/0.20 | 0.69 | $1.51 \times 10^{-4}$ | 0.28/0.33 |
| 6 | 32,789 | rs9275596 (C) | 0.14/0.22 | 0.56 | $1.91 \times 10^{-12}$ | 0.09/0.16 | 0.54 | $6.29 \times 10^{-8}$ | 0.20/0.27 |
| 6 | 32,917 | rs9357155 (A) | 0.15/0.20 | 0.69 | $5.19 \times 10^{-6}$ | 0.12/0.18 | 0.64 | $1.79 \times 10^{-5}$ | 0.11/0.13 |
| 6 | 32,919 | rs2071543 (A) | 0.16/0.22 | 0.70 | $7.19 \times 10^{-6}$ | 0.14/0.20 | 0.65 | $1.59 \times 10^{-5}$ | 0.12/0.14 |
| 6 | 33,194 | rs1883414 (T) | 0.19/0.24 | 0.73 | $3.26 \times 10^{-5}$ | 0.17/0.20 | 0.82 | $3.55 \times 10^{-2}$ | 0.29/0.33 |
| 6 | 33,205 | rs3129269 (T) | 0.21/0.27 | 0.73 | $1.32 \times 10^{-5}$ | 0.20/0.23 | 0.83 | $3.48 \times 10^{-2}$ | 0.33/0.38 |
| 22 | 28,824 | rs2412971 (A) | 0.31/0.39 | 0.72 | $8.21 \times 10^{-7}$ | 0.24/0.28 | 0.83 | $2.79 \times 10^{-2}$ | 0.46/0.51 |
| 22 | 28,859 | rs2412973 (A) | 0.32/0.39 | 0.73 | $1.91 \times 10^{-6}$ | 0.26/0.30 | 0.83 | $2.68 \times 10^{-2}$ | 0.46/0.51 |

| | European Replication Cohort[b] N = 2,410 (1,238 cases/1,172 controls) | | | All Cohorts Combined[b] N = 5,966 (3,144 cases/2,822 controls) | | | | |
|---|---|---|---|---|---|---|---|---|
| Chr | OR | P-value | Per allele | OR Het. | Hom. | P-value | Q | |
| 1 | 0.82 | $1.46 \times 10^{-2}$ | 0.77 | 0.79 | 0.45 | $4.24 \times 10^{-5}$ | 0.01* | |
| 1 | 0.71 | $1.19 \times 10^{-5}$ | 0.68 | 0.69 | 0.41 | $2.96 \times 10^{-10}$ | 0.17 | |
| 6 | 0.77 | $3.32 \times 10^{-6}$ | 0.73 | 0.69 | 0.59 | $8.44 \times 10^{-16}$ | 0.44 | |
| 6 | 0.70 | $7.40 \times 10^{-10}$ | 0.63 | 0.62 | 0.43 | $1.59 \times 10^{-26}$ | 0.31 | |
| 6 | 0.77 | $8.26 \times 10^{-4}$ | 0.71 | 0.66 | 0.62 | $2.11 \times 10^{-12}$ | 0.35 | |
| 6 | 0.81 | $1.66 \times 10^{-3}$ | 0.73 | 0.67 | 0.64 | $5.77 \times 10^{-12}$ | 0.27 | |
| 6 | 0.82 | $2.17 \times 10^{-4}$ | 0.78 | 0.77 | 0.61 | $4.84 \times 10^{-9}$ | 0.55 | |
| 6 | 0.83 | $6.67 \times 10^{-4}$ | 0.79 | 0.79 | 0.61 | $8.54 \times 10^{-9}$ | 0.42 | |
| 22 | 0.82 | $1.61 \times 10^{-3}$ | 0.80 | 0.75 | 0.66 | $1.86 \times 10^{-9}$ | 0.29 | |
| 22 | 0.83 | $2.09 \times 10^{-3}$ | 0.80 | 0.76 | 0.66 | $4.46 \times 10^{-9}$ | 0.28 | |

[a]Cochran-Armitage trend test;
[b]Stratified analysis using Mantel's extension of Cochran-Armitage trend test; Q: p-value for the Cochrane's Q statistic;
*significant heterogeneity ($P < 0.05$).
The per-allele, heterozygote and homozygote OR's are indicated for the combined cohort.

TABLE 3

Stepwise conditional analysis of association among the signals in the HLA region.

| | | Beijing Discovery Cohort N = 2,096 (1,194 cases/902 controls) | | Shanghai Follow-up Cohort N = 1,460 (712 cases/748 controls) | | European Follow-up Cohort N = 2,410 (1,238 cases/1,172 controls) | | All Cohorts Combined N = 5,966 (3,144 cases/2,822 controls) | |
|---|---|---|---|---|---|---|---|---|---|
| Test SNP | Conditioning SNR(s) | Unconditioned p-value | Conditioned p-value | Unconditioned p-value | Conditioned p-value | Unconditioned p-value | Conditioned p-value | Unconditioned p-value | Conditioned p-value |
| rs2856717 | rs9275596 | $3.30 \times 10^{-8}$ | 0.280 | $1.51 \times 10^{-4}$ | 0.271 | $3.32 \times 10^{-6}$ | 0.354 | $8.44 \times 10^{-16}$ | 0.114 |
| rs9275596 | | $1.91 \times 10^{-12}$ | NA | $6.29 \times 10^{-8}$ | NA | $7.40 \times 10^{-10}$ | NA | $1.59 \times 10^{-26}$ | NA |
| rs9357155 | | $5.19 \times 10^{-6}$ | $2.29 \times 10^{-3}$ | $1.79 \times 10^{-5}$ | $3.12 \times 10^{-4}$ | $8.26 \times 10^{-4}$ | $8.83 \times 10^{-4}$ | $2.11 \times 10^{-12}$ | $6.87 \times 10^{-9}$ |

TABLE 3-continued

Stepwise conditional analysis of association among the signals in the HLA region.

| Test SNP | Conditioning SNR(s) | Beijing Discovery Cohort N = 2,096 (1,194 cases/902 controls) | | Shanghai Follow-up Cohort N = 1,460 (712 cases/748 controls) | | European Follow-up Cohort N = 2,410 (1,238 cases/1,172 controls) | | All Cohorts Combined N = 5,966 (3,144 cases/2,822 controls) | |
|---|---|---|---|---|---|---|---|---|---|
| | | Unconditioned p-value | Conditioned p-value | Unconditioned p-value | Conditioned p-value | Unconditioned p-value | Conditioned p-value | Unconditioned p-value | Conditioned p-value |
| rs1883414 | | $1.32 \times 10^{-5}$ | $2.16 \times 10^{-4}$ | 0.0348 | 0.164 | $6.67 \times 10^{-4}$ | $3.64 \times 10^{-4}$ | $8.54 \times 10^{-9}$ | $9.94 \times 10^{-8}$ |
| rs2856717 | rs9275596, | $3.30 \times 10^{-8}$ | 0.236 | $1.51 \times 10^{-4}$ | 0.225 | $3.32 \times 10^{-6}$ | 0.303 | $8.44 \times 10^{-16}$ | 0.0754 |
| rs9275596 | rs357155 | $1.91 \times 10^{-12}$ | NA | $6.29 \times 10^{-8}$ | NA | $7.40 \times 10^{-10}$ | NA | $1.59 \times 10^{-26}$ | NA |
| rs9357155 | | $5.19 \times 10^{-6}$ | NA | $1.79 \times 10^{-5}$ | NA | $8.26 \times 10^{-4}$ | NA | $2.11 \times 10^{-12}$ | NA |
| rs1883414 | | $1.32 \times 10^{-5}$ | $7.04 \times 10^{-5}$ | 0.0348 | 0.059 | $6.67 \times 10^{-4}$ | $7.18 \times 10^{-4}$ | $8.54 \times 10^{-9}$ | $3.13 \times 10^{-8}$ |
| rs2856717 | rs9275596, | $3.30 \times 10^{-8}$ | 0.278 | $1.51 \times 10^{-4}$ | 0.241 | $3.32 \times 10^{-6}$ | 0.272 | $8.44 \times 10^{-16}$ | 0.0760 |
| rs9275596 | rs9357155, | $1.91 \times 10^{-12}$ | NA | $6.26 \times 10^{-8}$ | NA | $7.40 \times 10^{-10}$ | NA | $1.59 \times 10^{-26}$ | NA |
| rs9357155 | rs1883414 | $5.19 \times 10^{-6}$ | NA | $1.79 \times 10^{-5}$ | NA | $8.26 \times 10^{-4}$ | NA | $2.11 \times 10^{-12}$ | NA |
| rs1883414 | | $1.32 \times 10^{-5}$ | NA | 0.0348 | NA | $6.67 \times 10^{-4}$ | NA | $8.54 \times 10^{-9}$ | NA | rs9275596 and rs2856717 represent the major HLA signal near DQB1, rs9357155 and rs1883414 represent the other two independent signals in the HLA region.

TABLE 4

Cumulative effect of replicated loci stratrified by the number of protective alleles.

| No. of Protective Alleles | Beijing Discovery Cohort (N = 2,074)* 1,176 cases/898 controls | | | Asian Replication Cohort (N = 1,397)* 685 cases/712 controls | | |
|---|---|---|---|---|---|---|
| | Frequency (Cases/Controls) | Average Risk Score (+/− SD) | OR (95% CI) | Frequency (Cases/Controls) | Average Risk Score (+/− SD) | OR (95% CI) |
| 0 (highest risk) | 0.17/0.07 | 0.00 | 1.00 (reference) | 0.24/0.13 | 0.00 | 1.00 (reference) |
| 1 | 0.31/0.26 | −0.37 (+/−0.09) | 0.50 (0.36-0.69) | 0.38/0.32 | −0.30 (+/−0.15) | 0.66 (0.48-0.90) |
| 2 | 0.29/0.29 | −0.77 (+/−0.14) | 0.40 (0.29-0.56) | 0.24/0.31 | −0.65 (+/−0.23) | 0.43 (0.31-0.60) |
| 3 | 0.16/0.20 | −0.17 (+/−0.15) | 0.31 (0.22-0.44) | 0.10/0.14 | −1.06 (+/−0.26) | 0.40 (0.27-0.60) |
| 4 | 0.06/0.12 | −0.61 (+/−0.17) | 0.20 (0.13-0.31) | 0.04/0.08 | −1.44 (+/−0.28) | 0.28 (0.16-0.47) |
| ≥5 (lowest risk) | 0.01/0.06 | −2.11 (+/−0.25) | 0.09 (0.05-0.16) | 0.004/0.03 | −1.86 (+/−0.36) | 0.10 (0.03-0.33) |
| OR change highest vs. lowest risk[a] | | 11.1 | | | 10.0 | |
| P-value[b] | | $6.76 \times 10^{-27}$ | | | $3.13 \times 10^{-14}$ | |
| C-stat (95% CI)[c] | | 0.63 (0.60-0.65) | | | 0.61 (0.58-0.64) | |
| Nagelkerke R-sq[d] | | 0.072 | | | 0.054 | |

| No. of Protective Alleles | Asian Replication Cohort (N = 1,397)* 685 cases/712 controls OR (95% CI) | European Replication Cohort (N = 2,160)* 1,098 cases/1,062 controls | | |
|---|---|---|---|---|
| | | Frequency (Cases/Controls) | Average Risk Score (+/− SD) | OR (95% CI) |
| 0 (highest risk) | 1.00 (reference) | 0.07/0.03 | 0.00 | 1.00 (reference) |
| 1 | 0.66 (0.48-0.90) | 0.19/0.12 | −0.11 (+/−0.04) | 0.59 (0.36-0.97) |
| 2 | 0.43 (0.31-0.60) | 0.26/0.24 | −0.23 (+/−0.05) | 0.39 (0.25-0.63) |
| 3 | 0.40 (0.27-0.60) | 0.26/0.30 | −0.35 (+/−0.06) | 0.30 (0.19-0.48) |
| 4 | 0.28 (0.16-0.47) | 0.15/0.19 | −0.47 (+/−0.06) | 0.28 (0.17-0.45) |
| ≥5 (lowest risk) | 0.10 (0.03-0.33) | 0.08/0.13 | −0.65 (+/−0.10) | 0.21 (0.12-0.35) |
| OR change highest vs. lowest risk[a] | | | 4.8 | |
| P-value[b] | | | $6.24 \times 10^{-17}$ | |
| C-stat (95% CI)[c] | | | 0.60 (0.56-0.62) | |
| Nagelkerke R-sq[d] | | | 0.042 | |

*the risk scores were calculated based on the odds ratios and allele frequencies for each specific cohort Only individuals with non-missing genotypes for all 10 alleles were included in this analysis.
[a]Fold-change in odds ratio between highest and lowest risk group.
[b]P-value for the risk score prediction model.
[c]The C-statistic indicates the area under the receiver operating characteristic (ROC) curve for the risk score precdiction model.
[d]Nagelkerke's pseudo $R^2$ indicates the fraction of the variance in risk explained by the risk score model.

TABLE 5

Replication Study Results and Combined Meta-analysis. Combined association results for 12 SNPs representing 5 independent regions that reached genome-wide significance in the original GWAS. The combined effect estimates (per allele odds ratios) in the replication cohorts were all direction-consistent with the ones in the original GWAS cohorts. Significant heterogeneity was noted only for the second HLA locus represented by rs9357155 and rs2071543.

| | | | Replication Study N = 4,789 across 8 cohorts (2,228 cases/2,561 controls) | | | | | |
|---|---|---|---|---|---|---|---|---|
| Location | | SNP | Fixed Effects | | Random Effects# | | | |
| Chr | (kb) | (minor allele) | OR | P-value | OR | P-value | $I^2$ | Q-test |
| 1 | 194,918 | rs3766404 (C) | 0.78 | $2.5 \times 10^{-4}$ | 0.78 | $4.2 \times 10^{-4}$ | 0% | 0.84 (NS) |
| 1 | 194,953 | rs6677604 (A) | 0.78 | $3.1 \times 10^{-5}$ | 0.78 | $5.5 \times 10^{-5}$ | 0% | 0.48 (NS) |
| 6 | 32,768 | rs9275224 (A) | 0.75 | $3.6 \times 10^{-11}$ | 0.75 | $7.1 \times 10^{-11}$ | 0% | 0.67 (NS) |
| 6 | 32,778 | rs2856717 (T) | 0.86 | $1.1 \times 10^{-3}$ | 0.86 | $1.8 \times 10^{-3}$ | 0% | 0.71 (NS) |
| 6 | 32,779 | rs9275424 (G) | 1.22 | $5.0 \times 10^{-5}$ | 1.22 | $8.7 \times 10^{-5}$ | 19% | 0.27 (NS) |
| 6 | 32,789 | rs9275596 (C) | 0.75 | $5.3 \times 10^{-9}$ | 0.75 | $9.5 \times 10^{-9}$ | 0% | 0.60 (NS) |
| 6 | 32,917 | rs9357155 (A) | 0.96 | $5.8 \times 10^{-1}$ | 0.97 | $9.4 \times 10^{-2}$ | 54% | 0.025 * |
| 6 | 32,919 | rs2071543 (A) | 0.91 | $1.7 \times 10^{-1}$ | 0.92 | $1.2 \times 10^{-1}$ | 43% | 0.08 (NS) |
| 6 | 33,194 | rs1883414 (T) | 0.87 | $3.1 \times 10^{-3}$ | 0.87 | $5.0 \times 10^{-3}$ | 0% | 0.96 (NS) |
| 6 | 33,205 | rs3129269 (T) | 0.89 | $1.1 \times 10^{-2}$ | 0.89 | $1.7 \times 10^{-2}$ | 0% | 0.75 (NS) |
| 22 | 28,824 | rs2412971 (A) | 0.81 | $1.1 \times 10^{-8}$ | 0.81 | $2.1 \times 10^{-8}$ | 24% | 0.23 (NS) |
| 22 | 28,859 | rs2412973 (A) | 0.81 | $6.9 \times 10^{-7}$ | 0.81 | $1.2 \times 10^{-8}$ | 29% | 0.19 (NS) |

| Replication and GWAS N = 10,755 across 12 cohorts (5,372 cases/5,383 controls) | | | | | | | |
|---|---|---|---|---|---|---|---|
| | Fixed Effects | | Random Effects# | | | | Gene |
| Chr | OR | P-value | OR | P-value | $I^2$ | Q-test | Annotation |
| 1 | 0.78 | $7.9 \times 10^{-8}$ | 0.78 | $1.3 \times 10^{-7}$ | 6% | 0.39 (NS) | CFH, CFHR1, |
| 1 | 0.74 | $2.1 \times 10^{-13}$ | 0.74 | $4.6 \times 10^{-13}$ | 21% | 0.23 (NS) | CFHR3 |
| 6 | 0.72 | $8.5 \times 10^{-30}$ | 0.72 | $2.8 \times 10^{-29}$ | 0% | 0.69 (NS) | |
| 6 | 0.77 | $6.6 \times 10^{-18}$ | 0.78 | $7.3 \times 10^{-18}$ | 29% | 0.16 (NS) | HLA-DQB1, |
| 6 | 1.28 | $2.6 \times 10^{-14}$ | 1.26 | $4.6 \times 10^{-14}$ | 30% | 0.14 (NS) | -DQA1, -DRB1 |
| 6 | 0.67 | $5.0 \times 10^{-32}$ | 0.67 | $3.1 \times 10^{-32}$ | 43% | 0.05 (NS) | |
| 6 | 0.79 | $1.1 \times 10^{-8}$ | 0.87 | $2.6 \times 10^{-11}$ | 70% | $1.0 \times 10^{-4}$ ** | HLA-DOB, |
| 6 | 0.78 | $5.7 \times 10^{-10}$ | 0.84 | $4.0 \times 10^{-11}$ | 61% | $2.0 \times 10^{-3}$ ** | PSMB8, PSMB9, TAP1, TAP2 |
| 6 | 0.82 | $3.0 \times 10^{-10}$ | 0.82 | $5.9 \times 10^{-10}$ | 0% | 0.86 (NS) | HLA-DPB2, |
| 6 | 0.83 | $2.5 \times 10^{-9}$ | 0.83 | $4.6 \times 10^{-9}$ | 0% | 0.51 (NS) | -DRB1, -DRA1 |
| 22 | 0.80 | $4.0 \times 10^{-15}$ | 0.80 | $9.5 \times 10^{-15}$ | 12% | 0.33 (NS) | HORMAD2, |
| 22 | 0.80 | $9.9 \times 10^{-15}$ | 0.80 | $2.3 \times 10^{-14}$ | 16% | 0.29 (NS) | MTMR3, LIF, OSM, GATSL3, SF3A1 |

Q-test: P-value for the Cochrane's Q statistic for heterogeneity,
NS: heterogeneity test not significant,
* heterogeneity P < 0.05,
** heterogeneity P < 0.01;
$I^2$: Heterogeneity Index (0-100%), where <25% corresponds to low, 50%-75% to medium, and >75% to high level of heterogeneity;
OR: Additive (per-allele) Odds Ratio;
Han and Eskin random effects model.

TABLE 6

Conditional analysis of the HLA-DQB1, HLA-DQA1, HLA-DRB1 locus.

| | Replication Study N = 4,789 across 8 cohorts (2,228 cases/2,561 controls) | | | | Replication and GWAS N = 10,755 across 12 cohorts (5,372 cases/5,383 controls) | | | | |
|---|---|---|---|---|---|---|---|---|---|
| | UNADJUSTED | | CONDITIONED | | UNADJUSTED | | CONDITIONED | | |
| | OR | P-value | OR | P-value | OR | P-value | OR | P-value | CONDITIONING SNPs |
| rs9275224 | 0.75 | $4 \times 10^{-11}$ | 0.71 | $2 \times 10^{-6}$ | 0.72 | $9 \times 10^{-30}$ | 0.75 | $7 \times 10^{-10}$ | rs2856717, rs9275424, rs9275596 |
| rs2856717 | 0.86 | $1 \times 10^{-3}$ | 1.72 | $1 \times 10^{-6}$ | 0.77 | $7 \times 10^{-16}$ | 1.61 | $2 \times 10^{-10}$ | rs9275224, rs9275424, rs9275596 |
| rs9275424 | 1.22 | $5 \times 10^{-5}$ | 1.06 | $3 \times 10^{-1}$ | 1.28 | $3 \times 10^{-14}$ | 1.11 | $7 \times 10^{-3}$ | rs9275224, rs2856717, rs9275596 |
| rs9275596 | 0.75 | $5 \times 10^{-9}$ | 0.64 | $2 \times 10^{-6}$ | 0.67 | $5 \times 10^{-32}$ | 0.58 | $3 \times 10^{-16}$ | rs9275224, rs2856717, rs9275424 |

TABLE 7

Haplotype analysis of rs9275224, rs2856717, rs9275424, and r59275596 at the HLA-DQB1/DRB1 locus. The most common haplotype of 4 major alleles (GCAT) is used as a reference to derive odds ratios for all other haplotypes. Only common haplotypes (frequency >1%) are tested for association. All Cohorts: N = 10,755

| | Freq. Overall | Freq. Cases | Freq. Controls | OR | 95% CI | P-global |
|---|---|---|---|---|---|---|
| GCAT | 0.352 | 0.365 | 0.338 | -reference- | -reference- | $3 \times 10^{-43}$ |
| ATAC | 0.213 | 0.180 | 0.245 | 0.69 | 0.64-0.74 | |
| ACAT | 0.130 | 0.119 | 0.141 | 0.78 | 0.71-0.85 | |
| ATAT | 0.050 | 0.058 | 0.043 | 1.25 | 1.10-1.42 | |
| GCGT | 0.246 | 0.270 | 0.222 | 1.12 | 1.04-1.20 | |

TABLE 8

The comparison of the original and the newly refined IgAN risk score.

| | | Original Risk Score | | | | Newly Refined Risk Score | | | |
|---|---|---|---|---|---|---|---|---|---|
| Cohort: | N[#] | R²* | C** | OR*** | P-value**** | R²* | C** | OR*** | P-value**** |
| Original GWAS Cohorts | 5,631 | 5.0% | 0.61 | 1.51 | $3.1 \times 10^{-46}$ | 5.7% | 0.62 | 1.56 | $4.1 \times 10^{-52}$ |
| Replication Cohorts | 4,422 | 2.2% | 0.58 | 1.29 | $5.4 \times 10^{-17}$ | 3.2% | 0.59 | 1.36 | $3.3 \times 10^{-24}$ |
| Asian Cohorts Combined | 4,582 | 4.5% | 0.60 | 1.53 | $3.0 \times 10^{-34}$ | 5.0% | 0.61 | 1.52 | $2.6 \times 10^{-38}$ |
| European Cohorts Combined | 5,386 | 2.6% | 0.58 | 1.34 | $3.7 \times 10^{-24}$ | 3.6% | 0.59 | 1.42 | $6.7 \times 10^{-33}$ |
| All Cohorts Combined | 10,053 | 3.8% | 0.60 | 1.42 | $6.2 \times 10^{-63}$ | 4.7% | 0.61 | 1.47 | $1.2 \times 10^{-76}$ |

[#]Number of analyzed individuals with 100% non-missing genotypes across all 7 scored loci.
*R²: Nagelkerke R square (expressed as percentage)
**C-statistic: area under the ROC curve
***odds ratio per one standard deviation of the standardized risk score
****Wald's test for risk score as a quantitative predictor of disease status.

TABLE 9

Case-control association results for the individual replication cohorts.

| Loc Chr | (kb) | SNP (minor allele) | Italian Cohort N = 1,116 (478 cases/638 controls) | | French Cohort N = 895 (493 cases/402 controls) | | German Cohort N = 621 (249 cases/372 controls) | | Czech Cohort N = 465 (244 cases/221 controls) | |
|---|---|---|---|---|---|---|---|---|---|---|
| | | | OR | P-value | OR | P-value | OR | P-value | OR | P-value |
| 1 | 194,918 | rs3766404 (C) | 0.85 | $2.0 \times 10^{-1}$ | 0.72 | $6.4 \times 10^{-2}$ | 0.71 | $3.8 \times 10^{-2}$ | 1.01 | $9.5 \times 10^{-1}$ |
| 1 | 194,953 | rs6677604 (A) | 0.88 | $2.2 \times 10^{-1}$ | 0.70 | $4.3 \times 10^{-3}$ | 0.74 | $3.5 \times 10^{-2}$ | 1.02 | $9.2 \times 10^{-1}$ |
| 6 | 32,768 | rs9275224 (A) | 0.78 | $6.4 \times 10^{-3}$ | 0.76 | $4.7 \times 10^{-3}$ | 0.71 | $4.4 \times 10^{-3}$ | 0.84 | $2.3 \times 10^{-1}$ |
| 6 | 32,778 | rs2856717 (T) | 0.91 | $3.5 \times 10^{-1}$ | 0.89 | $2.7 \times 10^{-1}$ | 0.87 | $2.6 \times 10^{-1}$ | 0.89 | $3.6 \times 10^{-1}$ |
| 6 | 32,779 | rs9275424 (G) | 0.99 | $9.6 \times 10^{-1}$ | 1.36 | $6.0 \times 10^{-3}$ | 1.20 | $1.8 \times 10^{-1}$ | 1.21 | $2.5 \times 10^{-1}$ |
| 6 | 32,789 | rs9275596 (C) | 0.78 | $2.1 \times 10^{-2}$ | 0.82 | $6.5 \times 10^{-2}$ | 0.82 | $1.2 \times 10^{-1}$ | 0.73 | $6.7 \times 10^{-2}$ |
| 6 | 32,917 | rs9357155 (A) | 0.76 | $5.9 \times 10^{-2}$ | 1.23 | $1.6 \times 10^{-1}$ | 0.71 | $6.0 \times 10^{-2}$ | 0.79 | $2.4 \times 10^{-1}$ |
| 6 | 32,919 | rs2071543 (A) | 0.82 | $1.6 \times 10^{-1}$ | 1.11 | $4.7 \times 10^{-1}$ | 0.67 | $2.8 \times 10^{-2}$ | 0.71 | $1.1 \times 10^{-1}$ |
| 6 | 33,194 | rs1883414 (T) | 0.90 | $2.6 \times 10^{-1}$ | 0.84 | $8.1 \times 10^{-2}$ | 1.00 | $9.9 \times 10^{-1}$ | 0.80 | $1.2 \times 10^{-1}$ |
| 6 | 33,205 | rs3129269 (T) | 0.94 | $4.9 \times 10^{-1}$ | 0.92 | $4.1 \times 10^{-1}$ | 1.01 | $9.5 \times 10^{-1}$ | 0.76 | $5.7 \times 10^{-2}$ |
| 22 | 28,824 | rs2412971 (A) | 0.85 | $6.7 \times 10^{-2}$ | 0.81 | $2.2 \times 10^{-2}$ | 0.86 | $1.8 \times 10^{-1}$ | 0.92 | $5.1 \times 10^{-1}$ |
| 22 | 28,859 | rs2412973 (A) | 0.85 | $5.8 \times 10^{-2}$ | 0.79 | $1.4 \times 10^{-2}$ | 0.86 | $1.7 \times 10^{-1}$ | 0.93 | $5.5 \times 10^{-1}$ |

| Chr | Hungarian Cohort N = 431 (138 cases/293 controls) | | Chinese Cohort N = 617 (333 cases/284 controls) | | Japanese Cohort N = 550 (259 cases/291 controls) | | African-American Cohort N = 94 (34 cases/60 controls) | |
|---|---|---|---|---|---|---|---|---|
| | OR | P-value | OR | P-value | OR | P-value | OR | P-value |
| 1 | 0.79 | $2.7 \times 10^{-1}$ | 0.68 | $7.7 \times 10^{-2}$ | 0.72 | $1.8 \times 10^{-1}$ | 0.60 | $1.2 \times 10^{-1}$ |
| 1 | 0.73 | $9.4 \times 10^{-2}$ | 0.66 | $8.6 \times 10^{-2}$ | 0.71 | $2.6 \times 10^{-1}$ | 0.59 | $1.1 \times 10^{-1}$ |
| 6 | 0.60 | $9.5 \times 10^{-4}$ | 0.80 | $6.2 \times 10^{-2}$ | 0.74 | $1.8 \times 10^{-2}$ | 0.60 | $1.1 \times 10^{-1}$ |
| 6 | 0.65 | $6.7 \times 10^{-3}$ | 0.94 | $6.5 \times 10^{-1}$ | 0.76 | $9.7 \times 10^{-2}$ | 0.71 | $3.5 \times 10^{-1}$ |
| 6 | 1.37 | $9.6 \times 10^{-2}$ | 1.14 | $4.1 \times 10^{-1}$ | 1.47 | $2.6 \times 10^{-3}$ | 0.82 | $5.6 \times 10^{-1}$ |
| 6 | 0.58 | $1.2 \times 10^{-3}$ | 0.70 | $1.5 \times 10^{-2}$ | 0.66 | $3.9 \times 10^{-2}$ | 0.78 | $4.8 \times 10^{-1}$ |
| 6 | 1.59 | $5.4 \times 10^{-2}$ | 1.23 | $1.9 \times 10^{-1}$ | 0.83 | $3.2 \times 10^{-1}$ | 1.56 | $4.2 \times 10^{-1}$ |
| 6 | 1.58 | $5.3 \times 10^{-2}$ | 1.17 | $5.1 \times 10^{-1}$ | 0.80 | $2.1 \times 10^{-1}$ | 1.26 | $6.0 \times 10^{-1}$ |
| 6 | 0.90 | $5.1 \times 10^{-1}$ | 0.83 | $1.8 \times 10^{-1}$ | 0.84 | $2.5 \times 10^{-1}$ | 0.70 | $3.9 \times 10^{-1}$ |

TABLE 9-continued

Case-control association results for the individual replication cohorts.

| | | | | | | | | |
|---|---|---|---|---|---|---|---|---|
| 6 | 0.96 | $7.9 \times 10^{-1}$ | 0.82 | $1.5 \times 10^{-1}$ | 0.74 | $7.2 \times 10^{-2}$ | 0.74 | $4.4 \times 10^{-1}$ |
| 22 | 0.97 | $8.4 \times 10^{-1}$ | 0.72 | $9.5 \times 10^{-3}$ | 0.57 | $1.7 \times 10^{-4}$ | 0.62 | $1.3 \times 10^{-1}$ |
| 22 | 0.98 | $8.9 \times 10^{-1}$ | 0.72 | $9.8 \times 10^{-3}$ | 0.57 | $1.3 \times 10^{-4}$ | 0.62 | $1.3 \times 10^{-1}$ |

TABLE 10

Pairwise LD between the SNPs of the HLA region: r2 (top right half) and D' (bottom left half) for all cohorts (top), Europeans (middle) and Asians (bottom).

| | | | $r^2$ | | | |
|---|---|---|---|---|---|---|
| D' | rs9275224 | rs2856717 | rs9275424 | rs9275596 | rs9357155 | rs1883414 |
| All cohorts: N = 10,755 | | | | | | |
| rs9275224 | | 0.543 | 0.212 | 0.387 | 0.000 | 0.014 |
| rs2856717 | 0.998 | | 0.117 | 0.715 | 0.004 | 0.001 |
| rs9275424 | 0.997 | 0.997 | | 0.091 | 0.000 | 0.003 |
| rs9275596 | 0.946 | 0.947 | 0.993 | | 0.002 | 0.001 |
| rs9357155 | 0.049 | 0.101 | 0.013 | 0.066 | | 0.001 |
| rs1883414 | 0.159 | 0.030 | 0.163 | 0.039 | 0.108 | |
| European Cohorts: N = 5,938 | | | | | | |
| rs9275224 | | 0.623 | 0.205 | 0.451 | 0.005 | 0.000 |
| rs2856717 | 0.998 | | 0.130 | 0.715 | 0.000 | 0.002 |
| rs9275424 | 0.997 | 0.998 | | 0.104 | 0.007 | 0.000 |
| rs9275596 | 0.943 | 0.938 | 0.994 | | 0.002 | 0.002 |
| rs9357155 | 0.229 | 0.041 | 0.127 | 0.206 | | 0.003 |
| rs1883414 | 0.028 | 0.093 | 0.029 | 0.115 | 0.101 | |
| Asian Cohorts: N = 4,723 | | | | | | |
| rs9275224 | | 0.437 | 0.217 | 0.300 | 0.003 | 0.050 |
| rs2856717 | 0.997 | | 0.096 | 0.699 | 0.037 | 0.004 |
| rs9275424 | 0.998 | 1.000 | | 0.072 | 0.010 | 0.008 |
| rs9275596 | 0.950 | 0.959 | 0.995 | | 0.039 | 0.008 |
| rs9357155 | 0.102 | 0.224 | 0.381 | 0.200 | | 0.007 |
| rs1883414 | 0.343 | 0.065 | 0.286 | 0.105 | 0.381 | |

TABLE 11

The best predictive model for IgAN based on all the genotyped SNPs and their pairwise interaction terms. This model represents the solution of a stepwise logistic regression algorithm (BIC-based stepwise model selection). The coefficients from this model are used to refine the risk score for IgAN.

| | Best Predictive Model | | | | |
|---|---|---|---|---|---|
| Predictor (Reference Allele) | Coeficient (β) | OR (95% CI) | P-value | Chr. | Annotation of Genes in the Region |
| rs6677604 (A) | −0.49371 | 0.61 (0.53-0.71) | $2.2 \times 10^{-11}$ | 1q32 | CFH, CFHR1, CFHR3 |
| r59275224 (A) | −0.31307 | 0.73 (0.67-0.80) | $2.5 \times 10^{-11}$ | 6p21 | HLA-DQB1, -DQA1, -DRB1 (variant 1) |
| r52856717 (T) | 0.42265 | 1.53 (1.31-1.78) | $8.2 \times 10^{-8}$ | 6p21 | HLA-DQB1, -DQA1, -DRB1 (variant 2) |
| r59275596 (C) | −0.51157 | 0.60 (0.52-0.69) | $5.9 \times 10^{-13}$ | 6p21 | HLA-DQB1, -DQA1, -DRB1 (variant 3) |
| rs9357155 (A) | −0.28621 | 0.75 (0.69-0.82) | $3.8 \times 10^{-10}$ | 6p21 | HLA-DOB, PSMB8, PSMB9, TAP1, TAP2 |
| r51883414 (T) | −0.1805 | 0.83 (0.78-0.90) | $4.8 \times 10^{-7}$ | 6p21 | HLA-DPB2, -DPB1, -DPA1 |
| rs2412971 (A) | −0.28592 | 0.75 (0.70-0.81) | $2.3 \times 10^{-15}$ | 22q12 | HORMAD2, MTMR3, LIF, OSM, GATSL3, SF3A1 |
| rs6677604 (A) * rs2412971 (A) | 0.23171 | 1.26 (1.12-1.43) | $2.2 \times 10^{-4}$ | — | 1q32 by 22q12 interaction term |

TABLE 12

All possible 1$^{st}$ order multiplicative interactions between the 7 SNPs with independent effects on disease risk. Statistical significance is assessed using a Bonferroni-corrected threshold, alpha 0.05/21 = $2.4 \times 10^{-3}$.

| | | | | p-value | | | |
|---|---|---|---|---|---|---|---|
| beta | rs6677604 (A) | rs9275224 (A) | rs2856717 (T) | rs9275596 (C) | rs9357155 (A) | rs1883414 (T) | rs2412971 (A) |
| All cohorts: N = 10,755 | | | | | | | |
| rs6677604 (A) | | 0.80 (NS) | 0.08 (NS) | 0.13 (NS) | 0.62 (NS) | 0.89 (NS) | $2.5 \times 10^{-4}$*** |
| rs9275224 (A) | 0.01 | | 0.26 (NS) | 0.27 (NS) | 0.52 (NS) | 0.40 (NS) | 0.27 (NS) |

TABLE 12-continued

All possible 1$^{st}$ order multiplicative interactions between the 7 SNPs with independent effects on disease risk.
Statistical significance is assessed using a Bonferroni-corrected threshold, alpha 0.05/21 = 2.4 × 10$^{-3}$.

| | p-value | | | | | | |
|---|---|---|---|---|---|---|---|
| beta | rs6677604 (A) | rs9275224 (A) | rs2856717 (T) | rs9275596 (C) | rs9357155 (A) | rs1883414 (T) | rs2412971 (A) |
| rs2856717 (T) | 0.11 | 0.06 | | 0.36 (NS) | 0.90 (NS) | 0.01 (NS) | 0.02 (NS) |
| rs9275596 (C) | 0.10 | 0.06 | 0.05 | | 0.56 (NS) | 0.01 (NS) | 0.02 (NS) |
| rs9357155 (A) | 0.04 | 0.04 | 0.01 | −0.04 | | 0.25 (NS) | 0.09 (NS) |
| rs1883414 (T) | −0.01 | 0.04 | 0.13 | 0.14 | 0.07 | | 0.01 (NS) |
| rs2412971 (A) | 0.21 | 0.04 | 0.10 | 0.11 | 0.10 | 0.12 | |
| | | | European Cohorts: N = 5,938 | | | | |
| rs6677604 (A) | | 0.36 (NS) | 0.16 (NS) | 0.48 (NS) | 0.55 (NS) | 0.30 (NS) | 1.4 × 10$^{-3}$*** |
| rs9275224 (A) | 0.06 | | 0.77 (NS) | 0.96 (NS) | 0.74 (NS) | 0.37 (NS) | 0.10 (NS) |
| rs2856717 (T) | 0.10 | 0.02 | | 0.98 (NS) | 0.98 (NS) | 0.07 (NS) | 0.16 (NS) |
| rs9275596 (C) | 0.05 | 0.00 | 0.00 | | 0.59 (NS) | 0.12 (NS) | 0.39 (NS) |
| rs9357155 (Al | 0.06 | 0.01 | 0.00 | −0.05 | | 0.19 (NS) | 0.04 (NS) |
| rs1883414 (T) | −0.08 | 0.05 | 0.11 | 0.10 | 0.12 | | 0.06 (NS) |
| rs2412971 (A) | 0.22 | 0.09 | 0.08 | 0.05 | 0.17 | 0.11 | |
| | | | Asian Cohorts: N = 4,723 | | | | |
| rs6677604 (A) | | 0.15 (NS) | 0.71 (NS) | 0.96 (NS) | 0.23 (NS) | 0.72 (NS) | 0.60 (NS) |
| rs9275224 (A) | −0.20 | | 0.34 (NS) | 0.31 (NS) | 0.91 (NS) | 0.58 (NS) | 0.47 (NS) |
| rs2856717 (T) | −0.06 | 0.09 | | 0.75 (NS) | 0.78 (NS) | 0.24 (NS) | 0.54 (NS) |
| rs9275596 (C) | −0.01 | 0.10 | 0.04 | | 0.90 (NS) | 0.07 (NS) | 0.29 (NS) |
| rs9357155 (A) | −0.23 | 0.01 | −0.03 | −0.01 | | 0.96 (NS) | 0.61 (NS) |
| rs1883414 (T) | 0.06 | −0.04 | 0.10 | 0.16 | 0.01 | | 0.31 (NS) |
| rs2412971 (A) | 0.07 | −0.05 | 0.05 | 0.09 | −0.04 | 0.08 | |

TABLE 13

The comparison of the original and the newly refined genetic risk score.

| | | Original Risk Score | | | | Newly Refined Risk Score | | | |
|---|---|---|---|---|---|---|---|---|---|
| Cohort | N# | R$^2$* | C (95% CI)** | OR (95% CI)*** | P-value**** | R$^2$* | C (95% CI)** | OR (95% CI)*** | P-value**** |
| Italian Cohort | 1,005 | 2.0% | 0.57 (0.53-0.60) | 1.30 (1.14-1.49) | 1.5 × 10$^{-4}$ | 3.4% | 0.59 (0.56-0.63) | 1.43 (1.24-1.64) | 6.8 × 10$^{-7}$ |
| French Cohort | 859 | 1.8% | 0.57 (0.53-0.61) | 1.27 (1.10-1.45) | 7.6 × 10$^{-4}$ | 2.8% | 0.58 (0.55-0.62) | 1.36 (1.18-1.57) | 2.6 × 10$^{-5}$ |
| German Cohort | 571 | 2.3% | 0.58 (0.53-0.63) | 1.35 (1.12-1.62) | 1.9 × 10$^{-3}$ | 4.4% | 0.60 (0.56-0.65) | 1.54 (1.26-1.88) | 2.0 × 10$^{-5}$ |
| Czech Cohort | 402 | 1.7% | 0.57 (0.51-0.63) | 1.23 (1.03-1.46) | 2.4 × 10$^{-2}$ | 2.0% | 0.57 (0.52-0.63) | 1.23 (1.04-1.45) | 1.5 × 10$^{-2}$ |
| Hungarian Cohort | 393 | 2.8% | 0.59 (0.53-0.65) | 1.40 (1.10-1.79) | 5.7 × 10$^{-3}$ | 4.4% | 0.61 (0.55-0.67) | 1.54 (1.21-1.96) | 5.1 × 10$^{-4}$ |
| Chinese Cohort | 595 | 1.6% | 0.57 (0.52-0.62) | 1.29 (1.07-1.57) | 8.0 × 10$^{-3}$ | 2.7% | 0.59 (0.54-0.63) | 1.36 (1.14-1.62) | 6.2 × 10$^{-4}$ |
| Japanese Cohort | 512 | 2.7% | 0.59 (0.54-0.64) | 1.34 (1.12-1.60) | 1.5 × 10$^{-3}$ | 4.0% | 0.61 (0.56-0.65) | 1.38 (1.17-1.62) | 1.2 × 10$^{-4}$ |
| African-American Cohort | 85 | 4.6% | 0.63 (0.50-0.76) | 1.50 (0.93-2.41) | 9.6 × 10$^{-2}$ | 5.1% | 0.64 (0.51-0.77) | 1.63 (0.94-2.82) | 8.1 × 10$^{-2}$ |
| All Replication Cohorts | 4,422 | 2.2% | 0.58 (0.56-0.59) | 1.29 (1.22-1.37) | 5.4 × 10$^{-17}$ | 3.2% | 0.59 (0.57-0.61) | 1.36 (1.28-1.45) | 3.3 × 10$^{-24}$ |
| GWAS Discovery | 2,091 | 7.0% | 0.63 (0.60-0.65) | 1.70 (1.54-1.88) | 1.9 × 10$^{-24}$ | 7.6% | 0.64 (0.61-0.66) | 1.69 (1.54-1.86) | 1.5 × 10$^{-26}$ |
| GWAS Asian Follow-up | 1,384 | 5.3% | 0.61 (0.58-0.64) | 1.65 (1.44-1.89) | 5.8 × 10$^{-13}$ | 5.0% | 0.61 (0.58-0.64) | 1.57 (1.39-1.78) | 1.2 × 10$^{-12}$ |
| GWAS European Follow-up | 2,156 | 4.3% | 0.60 (0.58-0.63) | 1.46 (1.34-1.60) | 1.6 × 10$^{-16}$ | 5.3% | 0.61 (0.59-0.64) | 1.56 (1.42-1.71) | 1.0 × 10$^{-19}$ |
| All GWAS Cohorts | 5,631 | 5.0% | 0.61 (0.60-0.62) | 1.51 (1.43-1.60) | 3.1 × 10$^{-46}$ | 5.7% | 0.62 (0.60-0.63) | 1.56 (1.47-1.65) | 4.1 × 10$^{-52}$ |
| All Asian Cohorts Combined | 4,582 | 4.5% | 0.60 (0.59-0.62) | 1.53 (1.43-1.64) | 3.0 × 10$^{-34}$ | 5.0% | 0.61 (0.59-0.63) | 1.52 (1.43-1.62) | 2.6 × 10$^{-38}$ |
| All European Cohorts Combined | 5,386 | 2.6% | 0.58 (0.57-0.60) | 1.34 (1.26-1.41) | 3.7 × 10$^{-24}$ | 3.6% | 0.59 (0.58-0.61) | 1.42 (1.34-1.51) | 6.7 × 10$^{-33}$ |
| All Cohorts Combined | 10,053 | 3.8% | 0.60 (0.59-0.61) | 1.42 (1.36-1.50) | 6.2 × 10$^{-63}$ | 4.7% | 0.61 (0.60-0.62) | 1.47 (1.42-1.54) | 1.2 × 10$^{-76}$ |

Number of analyzed individuals with 100% non-missing genotypes across all 7 scored loci.
*R$^2$: Nagelkerke R square expressed as percent
**C-statistic: area under the ROC curve and its 95% confidence interval.
***odds ratio per one standard deviation of the standardized risk score and its 95% confidence interval.
****Wald's test for risk score as a quantitative predictor of disease status.

REFERENCES

1. Coresh, J. et al. Prevalence of chronic kidney disease in the United States. *JAMA* 298, 2038-47 (2007).
2. Tsukamoto, Y. et al. Report of the Asian Forum of Chronic Kidney Disease Initiative (AFCKDI) 2007. "Current status and perspective of CKD in Asia": diversity and specificity among Asian countries. *Clin Exp Nephrol* 13, 249-56 (2009).
3. Gesualdo, L., Di Palma, A. M., Morrone, L. F., Strippoli, G. F. & Schena, F. P. The Italian experience of the national registry of renal biopsies. *Kidney Int* 66, 890-4 (2004).
4. D'Amico, G. The commonest glomerulonephritis in the world: IgA nephropathy. *Q J Med* 64, 709-27 (1987).
5. Nair, R. & Walker, P. D. Is IgA nephropathy the commonest primary glomerulopathy among young adults in the USA. *Kidney Int* 69, 1455-8 (2006).

6. Varis, J. et al. Immunoglobulin and complement deposition in glomeruli of 756 subjects who had committed suicide or met with a violent death. *J Clin Pathol* 46, 607-10 (1993).
7. Suzuki, K. et al. Incidence of latent mesangial IgA deposition in renal allograft donors in Japan. *Kidney Int* 63, 2286-94 (2003).
8. Kiryluk, K. et al. Genetic studies of IgA nephropathy: past, present, and future. *Pediatr Nephrol* (2010).
9. Barratt, J. & Feehally, J. IgA nephropathy. *J Am Soc Nephrol* 16, 2088-97 (2005).
10. Hastings, M. C. et al. Galactose-Deficient IgA1 in African Americans with IgA Nephropathy: Serum Levels and Heritability. *Clin JAm Soc Nephrol* (2010).
11. Gharavi, A. G. et al. Aberrant IgA1 glycosylation is inherited in familial and sporadic IgA nephropathy. *J Am Soc Nephrol* 19, 1008-14 (2008).
12. Lin, X. et al. Aberrant galactosylation of IgA1 is involved in the genetic susceptibility of Chinese patients with IgA nephropathy. *Nephrol Dial Transplant* 24, 3372-5 (2009).
13. Moldoveanu, Z. et al. Patients with IgA nephropathy have increased serum galactose-deficient IgA1 levels. *Kidney Int* 71, 1148-54 (2007).
14. Mestecky, J. et al. Defective galactosylation and clearance of IgA1 molecules as a possible etiopathogenic factor in IgA nephropathy. *Contrib Nephrol* 104, 172-82 (1993).
15. Tomana, M. et al. Circulating immune complexes in IgA nephropathy consist of IgA1 with galactose-deficient hinge region and antiglycan antibodies. *J Clin Invest* 104, 73-81 (1999).
16. Gharavi, A.G. et al. IgA nephropathy, the most common cause of glomerulonephritis, is linked to 6q22-23. *Nat Genet* 26, 354-7 (2000).
17. Bisceglia, L. et al. Genetic heterogeneity in Italian families with IgA nephropathy: suggestive linkage for two novel IgA nephropathy loci. *Am J Hum Genet* 79, 1130-4 (2006).
18. Paterson, A. D. et al. Genome-wide linkage scan of a large family with IgA nephropathy localizes a novel susceptibility locus to chromosome 2q36. *J Am Soc Nephrol* 18, 2408-15 (2007).
19. Feehally, J. et al. HLA Has Strongest Association with IgA Nephropathy in Genome-Wide Analysis. *J Am Soc Nephrol* (2010).
20. Storey, J. D. & Tibshirani, R. Statistical significance for genomewide studies. *Proc Natl Acad Sci USA* 100, 9440-5 (2003).
21. de Bakker, P. I. et al. A high-resolution HLA and SNP haplotype map for disease association studies in the extended human MHC. *Nat Genet* 38, 1166-72 (2006).
22. Hughes, A. E. et al. A common CFH haplotype, with deletion of CFHR1 and CFHR3, is associated with lower risk of age-related macular degeneration. *Nat Genet* 38, 1173-7 (2006).
23. Raychaudhuri, S. et al. Associations of CFHR1-CFHR3 deletion and a CFH SNP to age-related macular degeneration are not independent. Nat Genet 42, 553-5; author reply 555-6 (2010).
24. Davila, S. et al. Genome-wide association study identifies variants in the CFH region associated with host susceptibility to meningococcal disease. *Nat Genet* 42, 772-6 (2010).
25. Barcellos, L. F. et al. High-density SNP screening of the major histocompatibility complex in systemic lupus erythematosus demonstrates strong evidence for independent susceptibility regions. *PLoS Genet* 5, e1000696 (2009).
26. Erlich, H. et al. HLA DR-DQ haplotypes and genotypes and type 1 diabetes risk: analysis of the type 1 diabetes genetics consortium families. *Diabetes* 57, 1084-92 (2008).
27. Ferreira, R. C. et al. Association of IFIH1 and other autoimmunity risk alleles with selective IgA deficiency. *Nat Genet* 42, 777-80 (2010).
28. Imielinski, M. et al. Common variants at five new loci associated with early-onset inflammatory bowel disease. *Nat Genet* 41, 1335-40 (2009).
29. Kamatani, Y. et al. A genome-wide association study identifies variants in the HLA-DP locus associated with chronic hepatitis B in Asians. *Nat Genet* 41, 591-5 (2009).
30. Singer, J. B. et al. A genome-wide study identifies HLA alleles associated with lumiracoxib-related liver injury. *Nat Genet* 42, 711-4 (2010).
31. Zhou, X. et al. HLA-DPB1 and DPB2 are genetic loci for systemic sclerosis: a genome-wide association study in Koreans with replication in North Americans. *Arthritis Rheum* 60, 3807-14 (2009).
32. Mignot, E. et al. Complex HLA-DR and -DQ interactions confer risk of narcolepsy-cataplexy in three ethnic groups. *Am J Hum Genet* 68, 686-99 (2001).
33. Begley, G. S., Horvath, A. R., Taylor, J. C. & Higgins, C. F. Cytoplasmic domains of the transporter associated with antigen processing and P-glycoprotein interact with subunits of the proteasome. *Mol Immunol* 42, 137-41 (2005).
34. Muchamuel, T. et al. A selective inhibitor of the immunoproteasome subunit LMP7 blocks cytokine production and attenuates progression of experimental arthritis. *Nat Med* 15, 781-7 (2009).
35. Coppo, R. et al. Upregulation of the immunoproteasome in peripheral blood mononuclear cells of patients with IgA nephropathy. *Kidney Int* 75, 536-41 (2009).
36. Atkinson, J.P. & Goodship, T.H. Complement factor H and the hemolytic uremic syndrome. *J Exp Med* 204, 1245-8 (2007).
37. Heinen, S. et al. Factor H-related protein 1 (CFHR-1) inhibits complement C5 convertase activity and terminal complex formation. *Blood* 114, 2439-47 (2009).
38. Esashi, E. et al. Oncostatin M deficiency leads to thymic hypoplasia, accumulation of apoptotic thymocytes and glomerulonephritis. *Eur J Immunol* 39, 1664-70 (2009).
39. Wojtasz, L. et al. Mouse HORMAD1 and HORMAD2, two conserved meiotic chromosomal proteins, are depleted from synapsed chromosome axes with the help of TRIP13 AAA-ATPase. *PLoS Genet* 5, e1000702 (2009).
40. Grossman, S. R. et al. A composite of multiple signals distinguishes causal variants in regions of positive selection. *Science* 327, 883-6 (2010).
41. Maller, J. et al. Common variation in three genes, including a noncoding variant in CFH, strongly influences risk of age-related macular degeneration. *Nat Genet* 38, 1055-9 (2006).
42. Genome-wide association study of 14,000 cases of seven common diseases and 3,000 shared controls. *Nature* 447, 661-78 (2007).
43. Zipfel, P. F. et al. Deletion of complement factor H-related genes CFHR1 and CFHR3 is associated with atypical hemolytic uremic syndrome. *PLoS Genet* 3, e41 (2007).
44. Purcell, S. et al. PLINK: a tool set for whole-genome association and population-based linkage analyses. *Am J Hum Genet* 81, 559-75 (2007).

45. Skol, A. D., Scott, L. J., Abecasis, G. R. & Boehnke, M. Joint analysis is more efficient than replication-based analysis for two-stage genome-wide association studies. *Nat Genet* 38, 209-13 (2006).
46. Clayton, D. & Leung, H.T. An R package for analysis of whole-genome association studies. *Hum Hered* 64, 45-51 (2007).
47. Browning, S. R. & Browning, B. L. Rapid and accurate haplotype phasing and missing-data inference for whole-genome association studies by use of localized haplotype clustering. *Am J Hum Genet* 81, 1084-97 (2007).
48. Gusev, A. et al. Whole population, genome-wide mapping of hidden relatedness. *Genome Res* 19, 318-26 (2009).
49. Conrad, D. F. et al. Origins and functional impact of copy number variation in the human genome. *Nature* 464, 704-12 (2010).
50. Craddock, N. et al. Genome-wide association study of CNVs in 16,000 cases of eight common diseases and 3,000 shared controls. *Nature* 464, 713-20 (2010).
51. US Patent Application 20100297660.
52. Yu-Hao Zhou et al., Steroids in the Treatment of IgA Nephropathy to the Improvement of Renal Survival: A Systematic Review and Meta-Analysis, PLoS ONE, April 2011, 6 (4), e18788, 1-10.
53. Ritsuko Katafuchi et al. The improvement of renal survival with steroid pulse therapy in IgA nephropathy, Nephrol Dial Transplant (2008) 23: 3915-3920.
54. Francesco Locatelli, et al., IgA nephritis: ACE inhibitors, steroids, both or neither?, Nephrol Dial Transplant (2006) 21: 3357-3361.
55. Norishige Yoshikawa, et al., Steroid Treatment for Severe Childhood IgA Nephropathy: A Randomized, Controlled Trial, Clin J Am Soc Nephrol 1: 511-517, 2006.

What is claimed is:

1. A method, comprising
a) obtaining a DNA sample from a subject,
b) a analyzing the DNA sample to detect the presence of one or more SNPs indicating a respective protective allele, wherein the SNPs analyzed comprise rs6677604, rs3766404, rs9275596, rs9275224, rs2856717, rs9357155, rs2071543, rs1883414, rs3129269, rs2412971, or rs2412973, or a combination thereof and
c) identifying the subject as not having at least one protective allele; and
d) treating the subject identified as not having at least one protective allele for IgAN.

2. The method of claim 1, further comprising calculating a genetic risk score comprising determining a weighted sum of the number the protective alleles in the DNA sample multiplied by the log of the odds ratio for each of the individual protective alleles.

3. The method of claim 1, wherein the subject has blood or protein, or both in the urine.

4. The method of claim 1, wherein treating the subject for IgAN comprises administering therapeutically effective amounts of one or more steroids.

5. The method of claim 1, further comprising calculating a genetic risk score based on the presence of one or more of the protective alleles.

6. The method of claim 5, further comprising analyzing an ethnicity of the subject, and wherein the odds ratio for each of the individual protected alleles is determined based on the ethnicity of the subject.

7. The method of claim 5, wherein the risk score is based on the presence of one or more alleles selected from the group of rs9275596, rs9357155, rs1883414, rs2412971, and rs6677604.

* * * * *